United States Patent
Bates et al.

(10) Patent No.: US 7,932,357 B2
(45) Date of Patent: Apr. 26, 2011

(54) FDF-03 S1 ANTIGEN-ANTIBODY COMPLEX

(75) Inventors: Elizabeth Bates, Lyons (FR); Nathalie Fournier, Villeurbanne (FR); Lionel Chalus, Lyons (FR); Pierre Garrone, Lyons (FR)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 10/780,043

(22) Filed: Feb. 17, 2004

(65) Prior Publication Data

US 2004/0137506 A1 Jul. 15, 2004

Related U.S. Application Data

(60) Division of application No. 09/869,388, filed as application No. PCT/US99/30004 on Dec. 29, 1999, now Pat. No. 6,774,214, which is a continuation-in-part of application No. 09/223,919, filed on Dec. 31, 1998, now abandoned, and a continuation-in-part of application No. 09/224,604, filed on Dec. 31, 1998, now abandoned.

(51) Int. Cl.
*C07K 16/00* (2006.01)
*C12P 21/08* (2006.01)
*C07K 1/00* (2006.01)

(52) U.S. Cl. ............ 530/387.1; 530/387.3; 530/388.1; 530/388.7; 530/389.1; 530/350

(58) Field of Classification Search .................. None
See application file for complete search history.

(56) References Cited

U.S. PATENT DOCUMENTS

| | | | | |
|---|---|---|---|---|
| 4,470,925 A | * | 9/1984 | Auditore-Hargreaves | 530/387.3 |
| 5,317,092 A | * | 5/1994 | Markussen | 530/413 |
| 6,774,214 B1 | | 8/2004 | Bates et al. | |
| 2002/0076761 A1 | * | 6/2002 | Escobedo et al. | 435/69.1 |
| 2005/0155089 A1 | * | 7/2005 | Lal et al. | 800/8 |

FOREIGN PATENT DOCUMENTS

| WO | WO 98/24906 | 6/1998 |
|---|---|---|
| WO | WO 98/25959 | 6/1998 |
| WO | WO 98/44113 | 10/1998 |
| WO | WO 99/18243 | 4/1999 |

OTHER PUBLICATIONS

Bost et al. Immunol. Invest. 1988; 17:577-586.*
Bendayan. J. Histochem. Cytochem. 1995; 43:881-886.*
Campbell. Monoclonal Antibody Technology. 1985 Published by Elsevier Science Publishers. Chapter I, pp. 1-32.*
Harlow et al. Antibodies. A Laboratory Manual. 1988, pp. 139-147 and 626-630.*

* cited by examiner

*Primary Examiner* — Chun Dahle
(74) *Attorney, Agent, or Firm* — Gregory R. Bellomy

(57) ABSTRACT

Nucleic acids encoding various monocyte-derived proteins and related compositions, including purified proteins and specific antibodies are described. Methods of using such composition are also provided.

6 Claims, No Drawings

SEQUENCE LISTING

```
<160> NUMBER OF SEQ ID NOS: 16

<210> SEQ ID NO 1
<211> LENGTH: 1249
<212> TYPE: DNA
<213> ORGANISM: Homo sapiens
<220> FEATURE:
<221> NAME/KEY: CDS
<222> LOCATION: (154)..(1062)
<220> FEATURE:
<221> NAME/KEY: sig_peptide
<222> LOCATION: (154)..(210)
<220> FEATURE:
<221> NAME/KEY: mat_peptide
<222> LOCATION: (211)..(1062)

<400> SEQUENCE: 1
gtttggggaa ggctcctggc ccccacagcc ctcttcggag cctgagcccg gctctcctca      60
ctcacctcaa ccccaggcg gcccctccac agggcccctc tcctgcctgg acggctctgc     120
```

```
tggtctcccc gtcccctgga gaagaacaag gcc atg ggt cgg ccc ctg ctg ctg        174
                                    Met Gly Arg Pro Leu Leu Leu
                                                    -15 ccc cta ctg ccc ctg ctg ctg ccg cca gca ttt ctg cag cct agt ggc        222
Pro Leu Leu Pro Leu Leu Leu Pro Pro Ala Phe Leu Gln Pro Ser Gly
        -10              -5                  -1  1 tcc aca gga tct ggt cca agc tac ctt tat ggg gtc act caa cca aaa        270
Ser Thr Gly Ser Gly Pro Ser Tyr Leu Tyr Gly Val Thr Gln Pro Lys
 5               10                  15                  20 cac ctc tca gcc tcc atg ggt ggc tct gtg gaa atc ccc ttc tcc ttc        318
His Leu Ser Ala Ser Met Gly Gly Ser Val Glu Ile Pro Phe Ser Phe
                     25                  30                  35 tat tac ccc tgg gag tta gcc aca gct ccc gac gtg aga ata tcc tgg        366
Tyr Tyr Pro Trp Glu Leu Ala Thr Ala Pro Asp Val Arg Ile Ser Trp
             40                  45                  50 aga cgg ggc cac ttc cac ggg cag tcc ttc tac agc aca agg ccg cct        414
Arg Arg Gly His Phe His Gly Gln Ser Phe Tyr Ser Thr Arg Pro Pro
         55                  60                  65 tcc att cac aag gat tat gtg aac cgg ctc ttt ctg aac tgg aca gag        462
Ser Ile His Lys Asp Tyr Val Asn Arg Leu Phe Leu Asn Trp Thr Glu
 70                  75                  80 ggt cag aag agc ggc ttc ctc agg atc tcc aac ctg cag aag cag gac        510
Gly Gln Lys Ser Gly Phe Leu Arg Ile Ser Asn Leu Gln Lys Gln Asp
85                   90                  95                 100 cag tct gtg tat ttc tgc cga gtt gag ctg gac aca cgg agc tca ggg        558
Gln Ser Val Tyr Phe Cys Arg Val Glu Leu Asp Thr Arg Ser Ser Gly
                 105                 110                 115 agg cag cag tgg cag tcc atc gag ggg acc aaa ctc tcc atc acc cag        606
Arg Gln Gln Trp Gln Ser Ile Glu Gly Thr Lys Leu Ser Ile Thr Gln
             120                 125                 130 gct gtc acg acc acc acc cag agg ccc agc agc atg act acc acc tgg        654
Ala Val Thr Thr Thr Thr Gln Arg Pro Ser Ser Met Thr Thr Thr Trp
         135                 140                 145 agg ctc agt agc aca acc acc aca acc ggc ctc agg gtc aca cag ggc        702
Arg Leu Ser Ser Thr Thr Thr Thr Thr Gly Leu Arg Val Thr Gln Gly
     150                 155                 160 aaa cga cgc tca gac tct tgg cac ata agt ctg gag act gct gtg ggg        750
Lys Arg Arg Ser Asp Ser Trp His Ile Ser Leu Glu Thr Ala Val Gly
165                 170                 175                 180 gtg gca gtg gct gtc act gtg ctc gga atc atg att ttg gga ctg atc        798
Val Ala Val Ala Val Thr Val Leu Gly Ile Met Ile Leu Gly Leu Ile
                 185                 190                 195 tgc ctc ctc agg tgg agg aga agg aaa ggt cag cag cgg act aaa gcc        846
Cys Leu Leu Arg Trp Arg Arg Arg Lys Gly Gln Gln Arg Thr Lys Ala
             200                 205                 210 aca acc cca gcc agg gaa ccc ttc caa aac aca gag gag cca tat gag        894
Thr Thr Pro Ala Arg Glu Pro Phe Gln Asn Thr Glu Glu Pro Tyr Glu
         215                 220                 225 aat atc agg aat gaa gga caa aat aca gat ccc aag cta aat ccc aag        942
Asn Ile Arg Asn Glu Gly Gln Asn Thr Asp Pro Lys Leu Asn Pro Lys
     230                 235                 240 gat gac ggc atc gta tat gct tcc ctt gcc ctc tcc agc tcc acc tca        990
Asp Asp Gly Ile Val Tyr Ala Ser Leu Ala Leu Ser Ser Ser Thr Ser
245                 250                 255                 260 ccc aga gca cct ccc agc cac cgt ccc ctc aag agc ccc cag aac gag       1038
Pro Arg Ala Pro Pro Ser His Arg Pro Leu Lys Ser Pro Gln Asn Glu
                 265                 270                 275 acc ctg tac tct gtc tta aag gcc taaccaatgg acagccctct caagactgaa      1092
Thr Leu Tyr Ser Val Leu Lys Ala
             280
```

```
tggtgaggcc aggtacagtg gcgcacacct gtaatcccag ctactctgaa gcctgaggca   1152
gaatcaagtg agcccaggag ttcagggcca gctttgataa tggagcgaga tgccatctct   1212
agttaaaaat atatattaac aataaagtaa caaattt                            1249
```

<210> SEQ ID NO 2
<211> LENGTH: 303
<212> TYPE: PRT
<213> ORGANISM: Homo sapiens

<400> SEQUENCE: 2

```
Met Gly Arg Pro Leu Leu Leu Pro Leu Leu Pro Leu Leu Leu Pro Pro
                -15                 -10                 -5

Ala Phe Leu Gln Pro Ser Gly Ser Thr Gly Ser Gly Pro Ser Tyr Leu
     -1   1               5                   10

Tyr Gly Val Thr Gln Pro Lys His Leu Ser Ala Ser Met Gly Gly Ser
     15                  20                  25

Val Glu Ile Pro Phe Ser Phe Tyr Tyr Pro Trp Glu Leu Ala Thr Ala
 30                  35                  40                  45

Pro Asp Val Arg Ile Ser Trp Arg Arg Gly His Phe His Gly Gln Ser
                 50                  55                  60

Phe Tyr Ser Thr Arg Pro Pro Ser Ile His Lys Asp Tyr Val Asn Arg
                 65                  70                  75

Leu Phe Leu Asn Trp Thr Glu Gly Gln Lys Ser Gly Phe Leu Arg Ile
                 80                  85                  90

Ser Asn Leu Gln Lys Gln Asp Gln Ser Val Tyr Phe Cys Arg Val Glu
                 95                 100                 105

Leu Asp Thr Arg Ser Ser Gly Arg Gln Gln Trp Gln Ser Ile Glu Gly
110                 115                 120                 125

Thr Lys Leu Ser Ile Thr Gln Ala Val Thr Thr Thr Gln Arg Pro
                130                 135                 140

Ser Ser Met Thr Thr Thr Trp Arg Leu Ser Ser Thr Thr Thr Thr Thr
                145                 150                 155

Gly Leu Arg Val Thr Gln Gly Lys Arg Arg Ser Asp Ser Trp His Ile
                160                 165                 170

Ser Leu Glu Thr Ala Val Gly Val Ala Val Ala Val Thr Val Leu Gly
                175                 180                 185

Ile Met Ile Leu Gly Leu Ile Cys Leu Leu Arg Trp Arg Arg Arg Lys
190                 195                 200                 205

Gly Gln Gln Arg Thr Lys Ala Thr Thr Pro Ala Arg Glu Pro Phe Gln
                210                 215                 220

Asn Thr Glu Glu Pro Tyr Glu Asn Ile Arg Asn Glu Gly Gln Asn Thr
                225                 230                 235

Asp Pro Lys Leu Asn Pro Lys Asp Asp Gly Ile Val Tyr Ala Ser Leu
                240                 245                 250

Ala Leu Ser Ser Ser Thr Ser Pro Arg Ala Pro Ser His Arg Pro
                255                 260                 265

Leu Lys Ser Pro Gln Asn Glu Thr Leu Tyr Ser Val Leu Lys Ala
270                 275                 280
```

<210> SEQ ID NO 3
<211> LENGTH: 943
<212> TYPE: DNA
<213> ORGANISM: Homo sapiens
<220> FEATURE:
<221> NAME/KEY: CDS
<222> LOCATION: (130)..(819)
<220> FEATURE:

```
<221> NAME/KEY: sig_peptide
<222> LOCATION: (130)..(180)
<220> FEATURE:
<221> NAME/KEY: mat_peptide
<222> LOCATION: (181)..(819)

<400> SEQUENCE: 3
acagccctct tcggagcctc agcccggctc tcctcactca cctcaacccc caggcggccc     60
ctccacaggg ccctctcct gcctggacgg ctctgctggt ctccccgtcc cctggagaag     120 aacaaggcc atg ggt cgg ccc ctg ctg ctg ccc cta ctg ccc ctg ctg ctg    171
          Met Gly Arg Pro Leu Leu Leu Pro Leu Leu Pro Leu Leu Leu
              -15              -10                 -5 ccg cca gca ttt ctg cag cct agt ggc tcc aca gga tct ggt cca agc      219
Pro Pro Ala Phe Leu Gln Pro Ser Gly Ser Thr Gly Ser Gly Pro Ser
         -1  1               5                  10 tac ctt tat ggg gtc act caa cca aaa cac ctc tca gcc tcc atg ggt      267
Tyr Leu Tyr Gly Val Thr Gln Pro Lys His Leu Ser Ala Ser Met Gly
    15                  20                  25 ggc tct gtg gaa atc ccc ttc tcc ttc tat tac ccc tgg gag tta gcc      315
Gly Ser Val Glu Ile Pro Phe Ser Phe Tyr Tyr Pro Trp Glu Leu Ala
30                  35                  40                  45 aca gct ccc gac gtg aga ata tcc tgg aga cgg ggc cac ttc cac ggg      363
Thr Ala Pro Asp Val Arg Ile Ser Trp Arg Arg Gly His Phe His Gly
                50                  55                  60 cag tcc ttc tac agc aca agg ccg cct tcc att cac aag gat tat gtg      411
Gln Ser Phe Tyr Ser Thr Arg Pro Pro Ser Ile His Lys Asp Tyr Val
            65                  70                  75 aac cgg ctc ttt ctg aac tgg aca gag ggt cag aag agc ggc ttc ctc      459
Asn Arg Leu Phe Leu Asn Trp Thr Glu Gly Gln Lys Ser Gly Phe Leu
        80                  85                  90 agg atc tcc aac ctg cag aag cag gac cag tct gtg tat ttc tgc cga      507
Arg Ile Ser Asn Leu Gln Lys Gln Asp Gln Ser Val Tyr Phe Cys Arg
    95                  100                 105 gtt gag ctg gac aca cgg agc tca ggg agg cag cag tgg cag tcc atc      555
Val Glu Leu Asp Thr Arg Ser Ser Gly Arg Gln Gln Trp Gln Ser Ile
110                 115                 120                 125 gag ggg acc aaa ctc tcc atc acc cag ggt cag cag cgg act aaa gcc      603
Glu Gly Thr Lys Leu Ser Ile Thr Gln Gly Gln Gln Arg Thr Lys Ala
                130                 135                 140 aca acc cca gcc agg gaa ccc ttc caa aac aca gag gag cca tat gag      651
Thr Thr Pro Ala Arg Glu Pro Phe Gln Asn Thr Glu Glu Pro Tyr Glu
            145                 150                 155 aat atc agg aat gaa gga caa aat aca gat ccc aag cta aat ccc aag      699
Asn Ile Arg Asn Glu Gly Gln Asn Thr Asp Pro Lys Leu Asn Pro Lys
        160                 165                 170 gat gac ggc atc gtc tat gct tcc ctt gcc ctc tcc agc tcc acc tca      747
Asp Asp Gly Ile Val Tyr Ala Ser Leu Ala Leu Ser Ser Ser Thr Ser
    175                 180                 185 ccc aga gca cct ccc agc cac cgt ccc ctc aag agc ccc cag aac gag      795
Pro Arg Ala Pro Pro Ser His Arg Pro Leu Lys Ser Pro Gln Asn Glu
190                 195                 200                 205 acc ctg tac tct gtc tta aag gcc taaccaatgg acagccctct caagactgaa    849
Thr Leu Tyr Ser Val Leu Lys Ala
                210 tggtgaggcc aggtacagtg gcgcacacct gtaatcccag ctactctgaa gcctgaggca    909 gaatcaagtg agcccaggag ttcagggcca gctt                                943

<210> SEQ ID NO 4
<211> LENGTH: 230
<212> TYPE: PRT
```

<213> ORGANISM: Homo sapiens

<400> SEQUENCE: 4

```
Met Gly Arg Pro Leu Leu Pro Leu Leu Pro Leu Leu Pro Pro
        -15              -10              -5
Ala Phe Leu Gln Pro Ser Gly Ser Thr Gly Ser Gly Pro Ser Tyr Leu
 -1   1               5                  10                  15
Tyr Gly Val Thr Gln Pro Lys His Leu Ser Ala Ser Met Gly Gly Ser
                 20                  25                  30
Val Glu Ile Pro Phe Ser Phe Tyr Tyr Pro Trp Glu Leu Ala Thr Ala
             35                  40                  45
Pro Asp Val Arg Ile Ser Trp Arg Arg Gly His Phe His Gly Gln Ser
         50                  55                  60
Phe Tyr Ser Thr Arg Pro Pro Ser Ile His Lys Asp Tyr Val Asn Arg
     65                  70                  75
Leu Phe Leu Asn Trp Thr Glu Gly Gln Lys Ser Gly Phe Leu Arg Ile
 80                  85                  90                  95
Ser Asn Leu Gln Lys Gln Asp Gln Ser Val Tyr Phe Cys Arg Val Glu
                100                 105                 110
Leu Asp Thr Arg Ser Ser Gly Arg Gln Gln Trp Gln Ser Ile Glu Gly
                115                 120                 125
Thr Lys Leu Ser Ile Thr Gln Gly Gln Arg Thr Lys Ala Thr Thr
                130                 135                 140
Pro Ala Arg Glu Pro Phe Gln Asn Thr Glu Glu Pro Tyr Glu Asn Ile
            145                 150                 155
Arg Asn Glu Gly Gln Asn Thr Asp Pro Lys Leu Asn Pro Lys Asp Asp
160                 165                 170                 175
Gly Ile Val Tyr Ala Ser Leu Ala Leu Ser Ser Ser Thr Ser Pro Arg
                180                 185                 190
Ala Pro Pro Ser His Arg Pro Leu Lys Ser Pro Gln Asn Glu Thr Leu
                195                 200                 205
Tyr Ser Val Leu Lys Ala
            210
```

```
<210> SEQ ID NO 5
<211> LENGTH: 1450
<212> TYPE: DNA
<213> ORGANISM: Homo sapiens
<220> FEATURE:
<221> NAME/KEY: CDS
<222> LOCATION: (386)..(1066)
<220> FEATURE:
<221> NAME/KEY: sig_peptide
<222> LOCATION: (386)..(436)
<220> FEATURE:
<221> NAME/KEY: mat_peptide
<222> LOCATION: (437)..(1066)
```

<400> SEQUENCE: 5

| | | |
|---|---|---|
| ccacgcgtcc ggcttctttg ggggtgaaga gattggggag gaatctccac ccctgggagg | 60 |
| cagaagccag gcatagcgcg ctggctagga ctccagtacc gtgaagggag gcagtgagag | 120 |
| cagacatctg tgcctcattc ctgatctcaa ggggaaagca agaacaaggg aggcttcctc | 180 |
| aggatctcga acctgcggaa ggaggaccag tctgtgtact tctgccaagt ccagctggac | 240 |
| atacagatca gggaggctgt cgtggcagtc atcaagggg acccacctca ccatcaccca | 300 |
| ggccctcagg cagcccctcc acagggcccc tctcctgcct ggacagctct gctggtctcc | 360 |

```
ccgtcccctg gagaagaaca aggcc atg ggt cgg ccc ctg ctg ctg ccc ctg          412
                              Met Gly Arg Pro Leu Leu Leu Pro Leu
                              -15                     -10 ctg ctc ctg ctg cag ccg cca gca ttt ctg cag cct ggt ggc tcc aca          460
Leu Leu Leu Leu Gln Pro Pro Ala Phe Leu Gln Pro Gly Gly Ser Thr
            -5              -1  1                   5 gga tct ggt cca agc tac ctt tat ggg gtc act caa cca aaa cac ctc          508
Gly Ser Gly Pro Ser Tyr Leu Tyr Gly Val Thr Gln Pro Lys His Leu
10                  15                  20 tca gcc tcc atg ggt ggc tct gtg gaa atc ccc ttc tcc ttc tat tac          556
Ser Ala Ser Met Gly Gly Ser Val Glu Ile Pro Phe Ser Phe Tyr Tyr
25                  30                  35                  40 ccc tgg gag tta gcc ata gtt ccc aac gtg aga ata tcc tgg aga cgg          604
Pro Trp Glu Leu Ala Ile Val Pro Asn Val Arg Ile Ser Trp Arg Arg
                45                  50                  55 ggc cac ttc cac ggg cag tcc ttc tac agc aca agg ccg cct tcc att          652
Gly His Phe His Gly Gln Ser Phe Tyr Ser Thr Arg Pro Pro Ser Ile
                60                  65                  70 cac aag gat tat gtg aac cgg ctc ttt ctg aac tgg aca gag ggt cag          700
His Lys Asp Tyr Val Asn Arg Leu Phe Leu Asn Trp Thr Glu Gly Gln
                75                  80                  85 gag agc ggc ttc ctc agg atc tca aac ctg cgg aag gag gac cag tct          748
Glu Ser Gly Phe Leu Arg Ile Ser Asn Leu Arg Lys Glu Asp Gln Ser
        90                  95                  100 gtg tat ttc tgc cga gtc gag ctg gac acc cgg aga tca ggg agg cag          796
Val Tyr Phe Cys Arg Val Glu Leu Asp Thr Arg Arg Ser Gly Arg Gln
105                 110                 115                 120 cag ttg cag tcc atc aag ggg acc aaa ctc acc atc acc cag gct gtc          844
Gln Leu Gln Ser Ile Lys Gly Thr Lys Leu Thr Ile Thr Gln Ala Val
                125                 130                 135 aca acc acc acc tgg agg ccc agc agc aca acc acc ata gcc ggc              892
Thr Thr Thr Thr Trp Arg Pro Ser Ser Thr Thr Thr Ile Ala Gly
                140                 145                 150 ctc agg gtc aca gaa agc aaa ggg cac tca gaa tca tgg cac cta agt          940
Leu Arg Val Thr Glu Ser Lys Gly His Ser Glu Ser Trp His Leu Ser
        155                 160                 165 ctg gac act gcc atc agg gtt gca ttg gct gtc gct gtg ctc aaa act          988
Leu Asp Thr Ala Ile Arg Val Ala Leu Ala Val Ala Val Leu Lys Thr
170                 175                 180 gtc att ttg gga ctg ctg tgc ctc ctc ctc tgg tgg agg aga agg               1036
Val Ile Leu Gly Leu Leu Cys Leu Leu Leu Trp Trp Arg Arg Arg
185                 190                 195                 200 aaa ggt agc agg gcg cca agc agt gac ttc tgaccaacag agtgtgggga            1086
Lys Gly Ser Arg Ala Pro Ser Ser Asp Phe
                205                 210 gaagggatgt gtattagccc cggaggacgt gatgtgagac ccgcttgtga gtcctccaca        1146
ctcgttcccc attggcaaga tacatggaga gcaccctgag gacctttaaa aggcaaagcc        1206
gcaaggcaga aggaggctgg gtccctgaat caccgactgg aggagagtta cctacaagag        1266
ccttcatcca ggagcatcca cactgcaatg atataggaat gaggtctgaa ctccactgaa        1326
ttaaaccact ggcatttggg ggctgtttat tatagcagtg caaagagttc ctttatcctc        1386
cccaaggatg gaaaaataca atttattttg cttaccataa aaaaaaaaaa aaaaaaaaa         1446 aaaa                                                                     1450

<210> SEQ ID NO 6
<211> LENGTH: 227
<212> TYPE: PRT
<213> ORGANISM: Homo sapiens
```

<400> SEQUENCE: 6

```
Met Gly Arg Pro Leu Leu Leu Pro Leu Leu Leu Leu Gln Pro Pro
        -15                 -10                  -5
Ala Phe Leu Gln Pro Gly Gly Ser Thr Gly Ser Gly Pro Ser Tyr Leu
 -1   1               5                  10                  15
Tyr Gly Val Thr Gln Pro Lys His Leu Ser Ala Ser Met Gly Gly Ser
                 20                  25                  30
Val Glu Ile Pro Phe Ser Phe Tyr Tyr Pro Trp Glu Leu Ala Ile Val
             35                  40                  45
Pro Asn Val Arg Ile Ser Trp Arg Arg Gly Phe His Gly Gln Ser
         50                  55                  60
Phe Tyr Ser Thr Arg Pro Pro Ser Ile His Lys Asp Tyr Val Asn Arg
     65                  70                  75
Leu Phe Leu Asn Trp Thr Glu Gly Gln Glu Ser Gly Phe Leu Arg Ile
 80                  85                  90                  95
Ser Asn Leu Arg Lys Glu Asp Gln Ser Val Tyr Phe Cys Arg Val Glu
                100                 105                 110
Leu Asp Thr Arg Arg Ser Gly Arg Gln Gln Leu Gln Ser Ile Lys Gly
                115                 120                 125
Thr Lys Leu Thr Ile Thr Gln Ala Val Thr Thr Thr Thr Trp Arg
            130                 135                 140
Pro Ser Ser Thr Thr Thr Ile Ala Gly Leu Arg Val Thr Glu Ser Lys
        145                 150                 155
Gly His Ser Glu Ser Trp His Leu Ser Leu Asp Thr Ala Ile Arg Val
160                 165                 170                 175
Ala Leu Ala Val Ala Val Leu Lys Thr Val Ile Leu Gly Leu Leu Cys
                180                 185                 190
Leu Leu Leu Leu Trp Trp Arg Arg Lys Gly Ser Arg Ala Pro Ser
                195                 200                 205
Ser Asp Phe
        210
```

<210> SEQ ID NO 7
<211> LENGTH: 909
<212> TYPE: DNA
<213> ORGANISM: Homo sapiens
<220> FEATURE:
<221> NAME/KEY: CDS
<222> LOCATION: (130)..(654)
<220> FEATURE:
<221> NAME/KEY: sig_peptide
<222> LOCATION: (130)..(180)
<220> FEATURE:
<221> NAME/KEY: mat_peptide
<222> LOCATION: (181)..(654)

<400> SEQUENCE: 7

```
acagccctct tcggagcctc agcccggctc tcctcactca cctcaacccc caggcggccc      60
ctccacaggg ccctctcct gcctggacgg ctctgctggt ctcccgtcc cctggagaag       120 aacaaggcc atg ggt cgg ccc ctg ctg ctg ccc cta ctg ccc ctg ctg ctg    171
          Met Gly Arg Pro Leu Leu Leu Pro Leu Leu Pro Leu Leu Leu
                   -15                 -10                  -5 ccg cca gca ttt ctg cag cct agt ggc tcc aca gga tct ggt cca agc      219
Pro Pro Ala Phe Leu Gln Pro Ser Gly Ser Thr Gly Ser Gly Pro Ser
        -1   1               5                  10 tac ctt tat ggg gtc act caa cca aaa cac ctc tca gcc tcc atg ggt      267
Tyr Leu Tyr Gly Val Thr Gln Pro Lys His Leu Ser Ala Ser Met Gly
        15                  20                  25
```

-continued

| | | |
|---|---|---|
| ggc tct gtg gaa atc ccc ttc tcc ttc tat tac ccc tgg gag tta gcc<br>Gly Ser Val Glu Ile Pro Phe Ser Phe Tyr Tyr Pro Trp Glu Leu Ala<br>30                           35                        40                        45 | | 315 |
| aca gct ccc gac gtg aga ata tcc tgg aga cgg ggc cac ttc cac ggg<br>Thr Ala Pro Asp Val Arg Ile Ser Trp Arg Arg Gly His Phe His Gly<br>                        50                        55                        60 | | 363 |
| cag tcc ttc tac agc aca agg ccg cct tcc att cac aag gat tat gtg<br>Gln Ser Phe Tyr Ser Thr Arg Pro Pro Ser Ile His Lys Asp Tyr Val<br>               65                        70                        75 | | 411 |
| aac cgg ctc ttt ctg aac tgg aca gag ggt cag aag agc ggc ttc ctc<br>Asn Arg Leu Phe Leu Asn Trp Thr Glu Gly Gln Lys Ser Gly Phe Leu<br>                    80                        85                        90 | | 459 |
| agg atc tcc aac ctg cag aag cag gac cag tct gtg tat ttc tgc cga<br>Arg Ile Ser Asn Leu Gln Lys Gln Asp Gln Ser Val Tyr Phe Cys Arg<br>95                          100                       105 | | 507 |
| gtt gag ctg gac aca cgg agc tca ggg agg cag cag tgg cag tcc atc<br>Val Glu Leu Asp Thr Arg Ser Ser Gly Arg Gln Gln Trp Gln Ser Ile<br>110                       115                     120                  125 | | 555 |
| gag ggg acc aaa ctc tcc atc acc cag ggg aac cct tcc aaa aca cag<br>Glu Gly Thr Lys Leu Ser Ile Thr Gln Gly Asn Pro Ser Lys Thr Gln<br>                        130                     135                  140 | | 603 |
| agg agc cat atg aga ata tca gga atg aag gac aaa ata cag atc cca<br>Arg Ser His Met Arg Ile Ser Gly Met Lys Asp Lys Ile Gln Ile Pro<br>                145                     150                  155 | | 651 |
| agc taaatccaa ggatgacggc atcgtctatg cttcccttgc cctctccagc<br>Ser | | 704 |
| tccacctcac ccagagcacc tcccagccac cgtcccctca agagccccca gaacgagacc | | 764 |
| ctgtactctg tcttaaaggc ctaaccaatg acagccctc tcaagactga atggtgaggc | | 824 |
| caggtacagt ggcgcacacc tgtaatccca gctactctga agcctgaggc agaatcaagt | | 884 |
| gagcccagga gttcagggcc agctt | | 909 |

```
<210> SEQ ID NO 8
<211> LENGTH: 175
<212> TYPE: PRT
<213> ORGANISM: Homo sapiens

<400> SEQUENCE: 8
```

Met Gly Arg Pro Leu Leu Pro Leu Leu Pro Leu Leu Pro Pro
        -15                      -10                            -5

Ala Phe Leu Gln Pro Ser Gly Ser Thr Gly Ser Gly Pro Ser Tyr Leu
-1  1                  5                       10                       15

Tyr Gly Val Thr Gln Pro Lys His Leu Ser Ala Ser Met Gly Gly Ser
                20                        25                        30

Val Glu Ile Pro Phe Ser Phe Tyr Tyr Pro Trp Glu Leu Ala Thr Ala
                35                        40                        45

Pro Asp Val Arg Ile Ser Trp Arg Arg Gly His Phe His Gly Gln Ser
                50                        55                        60

Phe Tyr Ser Thr Arg Pro Pro Ser Ile His Lys Asp Tyr Val Asn Arg
                65                        70                        75

Leu Phe Leu Asn Trp Thr Glu Gly Gln Lys Ser Gly Phe Leu Arg Ile
80                         85                       90                       95

Ser Asn Leu Gln Lys Gln Asp Gln Ser Val Tyr Phe Cys Arg Val Glu
                100                     105                   110

Leu Asp Thr Arg Ser Ser Gly Arg Gln Gln Trp Gln Ser Ile Glu Gly
                115                     120                   125

```
Thr Lys Leu Ser Ile Thr Gln Gly Asn Pro Lys Thr Gln Arg Ser
        130                 135                 140

His Met Arg Ile Ser Gly Met Lys Asp Lys Ile Gln Ile Pro Ser
    145                 150                 155

<210> SEQ ID NO 9
<211> LENGTH: 1459
<212> TYPE: DNA
<213> ORGANISM: Homo sapiens
<220> FEATURE:
<221> NAME/KEY: CDS
<222> LOCATION: (309)..(986)
<220> FEATURE:
<221> NAME/KEY: sig_peptide
<222> LOCATION: (309)..(359)
<220> FEATURE:
<221> NAME/KEY: mat_peptide
<222> LOCATION: (309)..(986)

<400> SEQUENCE: 9
ggcacgacgc cccatctcta ctaataaaaa aaaaaaaaaa ggatttgaag tcctggccgg      60
agcaattagg caagggataa aaaggcacct aaggcccttt tgcaataaga agccagatgg     120
ataaaggaag tgctggtcac cctggaggtg tactggtttg gggaaggtcc ccggccccca     180
cagccctctg gggagcctca ccctggctct ccccactcac ctcagccctc aggcagcccc     240
tccacaggac ccctctcctg cctggacagc tctgctggtc tccccgtccc ctggagaaga     300
```

| acaaggcc atg ggt cgg ccc ctg ctg ctg ccc ctg ctg ctc ctg ctg cag | 350 |
|---|---|
|            Met Gly Arg Pro Leu Leu Leu Pro Leu Leu Leu Leu Leu Gln | |
|             1         5                10 | |

```
ccg cca gca ttt ctg cag cct ggt ggc tcc aca gga tct ggt cca agc      398
Pro Pro Ala Phe Leu Gln Pro Gly Gly Ser Thr Gly Ser Gly Pro Ser
15                  20                  25                  30 tac ctt tat ggg gtc act caa cca aaa cac ctc tca gcc tcc atg ggt      446
Tyr Leu Tyr Gly Val Thr Gln Pro Lys His Leu Ser Ala Ser Met Gly
                35                  40                  45 ggc tct gtg gaa atc ccc ttc tcc ttc tat tac ccc tgg gag tta gcc      494
Gly Ser Val Glu Ile Pro Phe Ser Phe Tyr Tyr Pro Trp Glu Leu Ala
            50                  55                  60 aca gct ccc gac gtg aga ata tcc tgg aga cgg ggc cac ttc cac ggg      542
Thr Ala Pro Asp Val Arg Ile Ser Trp Arg Arg Gly His Phe His Gly
65                  70                  75 cag tcc ttc tac agc aca agg ccg cct tcc att cac aag gat tat gtg      590
Gln Ser Phe Tyr Ser Thr Arg Pro Pro Ser Ile His Lys Asp Tyr Val
        80                  85                  90 aac cgg ctc ttt ctg aac tgg aca gag ggt cag gag agc ggc ttc ctc      638
Asn Arg Leu Phe Leu Asn Trp Thr Glu Gly Gln Glu Ser Gly Phe Leu
95                  100                 105                 110 agg atc tca aac ctg cgg aag gag gac cag tct gtg tat ttc tgc cga      686
Arg Ile Ser Asn Leu Arg Lys Glu Asp Gln Ser Val Tyr Phe Cys Arg
                115                 120                 125 gtc gag ctg gac acc cgg aga tca ggg agg cag cag ttg cag tcc atc      734
Val Glu Leu Asp Thr Arg Arg Ser Gly Arg Gln Gln Leu Gln Ser Ile
            130                 135                 140 aag ggg acc aaa ctc acc atc acc cag gct gtc aca acc acc acc acc      782
Lys Gly Thr Lys Leu Thr Ile Thr Gln Ala Val Thr Thr Thr Thr Thr
145                 150                 155 tgg agg ccc agc agc aca acc acc ata gcc ggc ctc agg gtc aca gaa      830
Trp Arg Pro Ser Ser Thr Thr Thr Ile Ala Gly Leu Arg Val Thr Glu
        160                 165                 170
```

```
agc aaa ggg cac tca gaa tca tgg cac cta agt ctg gac act gcc atc    878
Ser Lys Gly His Ser Glu Ser Trp His Leu Ser Leu Asp Thr Ala Ile
175                 180                 185                 190 agg gtt gca ttg gct gtc gct gtg ctc aaa act gtc att ttg gga ctg    926
Arg Val Ala Leu Ala Val Ala Val Leu Lys Thr Val Ile Leu Gly Leu
                195                 200                 205 ctg tgc ctc ctc ctg tgg tgg agg aga agg aaa ggt agc agg gcg cca    974
Leu Cys Leu Leu Leu Trp Trp Arg Arg Arg Lys Gly Ser Arg Ala Pro
            210                 215                 220 agc agt gac ttc tgaccaacag agtgtgggga aagggatgt gtattagccc        1026
Ser Ser Asp Phe
            225 cggaggacgt gatgtgagac ccgcttgtga gtcctccaca ctcgttcccc attggcaaga    1086 tacatggaga gcaccctgag gacctttaaa aggcaaagcc gcaaggcaga aggaggctgg    1146 gtccctgaat caccgactgg aggagagtta cctacaagag ccttcatcca ggagcatcca    1206 cactgcaatg atataggaat gaggtctgaa ctccactgaa ttaaaccact ggcatttggg    1266 ggctgttcat tatagcagtg caaagagttc ctttatcctc cccaaggatg aaaatacaa    1326 tttattttgc ttaccataca ccccttttct cctcgtccac attttccaat ctgtatggtg    1386 gctgtcttct atggcagaag gttttgggga ataaatagcg tgaaatgctg ctgaaaaaaa    1446 aaaaaaaaaa aaa                                                      1459

<210> SEQ ID NO 10
<211> LENGTH: 226
<212> TYPE: PRT
<213> ORGANISM: Homo sapiens

<400> SEQUENCE: 10

Met Gly Arg Pro Leu Leu Pro Leu Leu Leu Leu Gln Pro Pro
1               5                   10                  15

Ala Phe Leu Gln Pro Gly Gly Ser Thr Gly Ser Gly Pro Ser Tyr Leu
                20                  25                  30

Tyr Gly Val Thr Gln Pro Lys His Leu Ser Ala Ser Met Gly Gly Ser
            35                  40                  45

Val Glu Ile Pro Phe Ser Phe Tyr Tyr Pro Trp Glu Leu Ala Thr Ala
    50                  55                  60

Pro Asp Val Arg Ile Ser Trp Arg Arg Gly His Phe His Gly Gln Ser
65                  70                  75                  80

Phe Tyr Ser Thr Arg Pro Pro Ser Ile His Lys Asp Tyr Val Asn Arg
                85                  90                  95

Leu Phe Leu Asn Trp Thr Glu Gly Gln Glu Ser Gly Phe Leu Arg Ile
                100                 105                 110

Ser Asn Leu Arg Lys Glu Asp Gln Ser Val Tyr Phe Cys Arg Val Glu
            115                 120                 125

Leu Asp Thr Arg Arg Ser Gly Arg Gln Gln Leu Gln Ser Ile Lys Gly
        130                 135                 140

Thr Lys Leu Thr Ile Thr Gln Ala Val Thr Thr Thr Thr Trp Arg
145                 150                 155                 160

Pro Ser Ser Thr Thr Thr Ile Ala Gly Leu Arg Val Thr Glu Ser Lys
                165                 170                 175

Gly His Ser Glu Ser Trp His Leu Ser Leu Asp Thr Ala Ile Arg Val
            180                 185                 190

Ala Leu Ala Val Ala Val Leu Lys Thr Val Ile Leu Gly Leu Leu Cys
        195                 200                 205
```

Leu Leu Leu Trp Trp Arg Arg Arg Lys Gly Ser Arg Ala Pro Ser Ser
            210                 215                 220

Asp Phe
225

<210> SEQ ID NO 11
<211> LENGTH: 21
<212> TYPE: DNA
<213> ORGANISM: Homo sapiens

<400> SEQUENCE: 11
acagccctct tcggagcctc a                                            21

<210> SEQ ID NO 12
<211> LENGTH: 21
<212> TYPE: DNA
<213> ORGANISM: Homo sapiens

<400> SEQUENCE: 12
aagctggccc tgaactcctg g                                            21

<210> SEQ ID NO 13
<211> LENGTH: 18
<212> TYPE: DNA
<213> ORGANISM: Homo sapiens

<400> SEQUENCE: 13
caagggataa aaaggcac                                                18

<210> SEQ ID NO 14
<211> LENGTH: 18
<212> TYPE: DNA
<213> ORGANISM: Homo sapiens

<400> SEQUENCE: 14
aactctcctc cagtcggt                                                18

<210> SEQ ID NO 15
<211> LENGTH: 126
<212> TYPE: PRT
<213> ORGANISM: Homo sapiens

<400> SEQUENCE: 15

Gln Val Gln Leu Gln Glu Ser Gly Pro Gly Leu Val Lys Pro Ser Glu
1               5                   10                  15

Thr Leu Ser Leu Thr Cys Thr Val Ser Gly Gly Ser Val Ser Ser Gly
            20                  25                  30

Ser Tyr Tyr Trp Ser Trp Ile Arg Gln Ala Pro Gly Lys Gly Leu Glu
        35                  40                  45

Trp Ile Gly Tyr Ile Tyr Tyr Ser Gly Ser Thr Asn Tyr Asn Arg Ser
    50                  55                  60

His Lys Ser Arg Val Asn Ile Ser Val Asp Thr Ala Lys Asn Gln Phe
65                  70                  75                  80

Ser Leu Lys Leu Ser Ser Val Thr Ala Asp Thr Ala Val Tyr Tyr
                85                  90                  95

Cys Ala Arg Ile Thr Thr Thr Val Pro Ser Ser Trp Tyr Tyr Tyr Tyr
            100                 105                 110

Met Asp Val Trp Asp Lys Gly Thr Thr Val Thr Val Ser Ser
            115                 120                 125

<210> SEQ ID NO 16
<211> LENGTH: 121
<212> TYPE: PRT
<213> ORGANISM: Homo sapiens

<400> SEQUENCE: 16

```
Gln Val Gln Leu Gln Glu Ser Gly Pro Gly Leu Val Lys Pro Ser Glu
1               5                   10                  15

Thr Leu Ser Leu Thr Cys Thr Val Ser Gly Tyr Ser Ile Ser Ser Gly
            20                  25                  30

Tyr Tyr Trp Gly Trp Ile Arg Gln Pro Pro Gly Lys Gly Leu Glu Trp
        35                  40                  45

Ile Gly Ser Ile Tyr His Ser Gly Ser Thr Tyr Tyr Asn Pro Ser Leu
    50                  55                  60

Lys Ser Arg Val Thr Ile Ser Val Asp Thr Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Val Arg Arg Arg Tyr Ser Ser Ser Ala Ser Lys Ile Ile Phe
            100                 105                 110

Gly Ser Gly Thr Arg Leu Ser Ile Arg
            115                 120
```

FDF-03 S1 ANTIGEN-ANTIBODY COMPLEX

This application is a divisional of U.S. application Ser. No. 09/869,388, filed Oct. 9, 2001, now U.S. Pat. No. 6,774,214, which is the U.S. National Phase application of international patent Application No. PCT/US99/30004, filed Dec. 29, 1999, which is a continuation-in-part of application Ser. No. 09/223,919, filed Dec. 31, 1998, now abandoned, and is also a continuation-in-part of application Ser. No. 09/224,604, filed Dec. 31, 1998, now abandoned.

FIELD OF THE INVENTION

The present invention is directed to compositions related to genes found in monocytes, cells which function in the immune system. These genes function in controlling development, differentiation, and/or physiology of the mammalian immune system. In particular, the invention provides nucleic acids, proteins, antibodies, and methods of using them.

BACKGROUND OF THE INVENTION

Monocytes are phagocytic cells that belong to the mononuclear phagocyte system and reside in the circulation. These cells originate in the bone marrow and remain only a short time in the marrow compartment once they differentiate. They then enter the circulation and can remain there for a relatively long period of time, e.g., a few days. Monocytes can enter the tissues and body cavities by a process known as diapedesis, where they differentiate into macrophages and possibly into dendritic cells. In an inflammatory response, the number of monocytes in the circulation may double, and many of the increased number of monocytes diapedese to the site of inflammation. For a review of monocytes and their functions, see, e.g., Gallin, et al. (eds), 1988, *Inflammation: Basic Principles and Clinical Correlates*, Raven Press, NY; van Furth (ed), 1985, *Mononuclear Phagocytes: Characteristics, Physiology and Function*, Martinus Nijhoff, Dordrecht, Netherlands.

Antigen presentation refers to the cellular events in which a proteinaceous antigen is taken up, processed by antigen presenting cells (APC), and then recognized to initiate an immune response. The most active antigen presenting cells have been characterized as the macrophages, which are direct developmental products from monocytes; dendritic cells; and certain B cells.

Macrophages are found in most tissues and are highly active in internalization of a wide variety of protein antigens and microorganisms. They have a highly developed endocytic activity, and secrete many products important in the initiation of an immune response. For this reason, it is believed that many genes expressed by monocytes or induced by monocyte activation are important in antigen uptake, processing, presentation, or regulation of the resulting immune response.

Despite the importance of monocytes to immune system function, these cells remain poorly characterized, both in terms of the proteins they express and in terms of many of their functions, in particular, the processes and mechanisms related to the initiation of an immune response, including antigen processing and presentation. There is thus a need in the art for agents useful in the diagnosis and treatment of medical conditions caused by, e.g., the inappropriate regulation, development, or physiology of antigen presenting cells.

SUMMARY OF THE INVENTION

The present invention fulfills this need by providing compositions and methods for determining the presence, amount, distribution and normalcy of certain gene products and for facilitating the discovery of agents for treating certain disease states.

The invention is based upon the discovery of novel genes and gene products isolated from activated monocytes.

The invention provides isolated nucleic acid sequences comprising at least about 12, preferably at least about 18, most preferably at least about 20-35, and most preferably 35-55 or more consecutive nucleotides shown in SEQ ID NO: 1, 3, 5, 7, or 9, or which encode an amino acid sequence shown in SEQ ID NO: 2, 4, 6, 8 or 10, including complete protein coding sequences, and complements thereof. The invention encompasses sequence-conservative variants and function-conservative variants of these sequences. The nucleic acids may be DNA, RNA, DNA/RNA duplexes, protein-nucleic acid (PNA), or derivatives thereof. The invention also encompasses recombinant DNA vectors (including DNA expression vectors) comprising these sequences; cells comprising such vectors, including bacterial, fungal, plant, insect, and mammalian cells; and methods for producing expression products comprising RNA and polypeptides encoded by the sequences.

Polypeptide sequences of the invention comprise at least eight, preferably at least about 10, and more preferably at least about 12 or more consecutive amino acid residues derived from SEQ ID NO: 2, 4, 6, 8 or 10. Function-conservative variants and homologs are included in the scope of the invention.

The invention further provides binding compositions, in particular antibodies, most particularly monoclonal antibodies, which specifically bind to polypeptides having an amino acid sequence shown in SEQ ID NO: 2, 4, 6, 8 or 10 or function conserved variants or homologs thereof. Methods are also provided for producing antibodies having the desired binding specificity in a host animal.

DETAILED DESCRIPTION OF THE INVENTION

All patent applications, patents, and literature references cited in this specification are hereby incorporated herein by reference in their entirety.

In practicing the present invention, many conventional techniques in molecular biology, microbiology, and recombinant DNA, are used. Such techniques are well known and are explained fully in, for example, Sambrook et al., 1989, *Molecular Cloning: A Laboratory Manual*, Second Edition, Cold Spring Harbor Laboratory Press, Cold Spring Harbor, New York; *DNA Cloning: A Practical Approach*, Volumes I and II, 1985 (D. N. Glover ed.); *Oligonucleotide Synthesis*, 1984, (M. L. Gait ed.); *Nucleic Acid Hybridization*, 1985, (Hames and Higgins); *Transcription and Translation*, 1984 (Hames and Higgins eds.); Animal Cell Culture, 1986 (R. I. Freshney ed.); *Immobilized Cells and Enzymes*, 1986 (IRL Press); Perbal, 1984, *A Practical Guide to Molecular Cloning*; the series, *Methods in Enzymology* (Academic Press, Inc.); *Gene Transfer Vectors for Mammalian Cells*, 1987 (J. H. Miller and M. P. Calos eds., Cold Spring Harbor Laboratory); and *Methods in Enzymology* Vol. 154 and Vol. 155 (Wu and Grossman, and Wu, eds., respectively).

Definitions

1. A "monocyte-derived" nucleic acid or polypeptide refers to the source from which the sequence was originally isolated.

2. "Nucleic acid" or "polynucleotide" refers to purine- and pyrimidine-containing polymers of any length, either polyribonucleotides or polydeoxyribonucleotides or mixed polyribo-polydeoxyribo nucleotides. This includes singleand double-stranded molecules, i.e., DNA-DNA, DNA-RNA and RNA-RNA hybrids, as well as "protein nucleic acids" (PNA) formed by conjugating bases to an amino acid backbone. This also includes nucleic acids containing modified bases.

3. A "coding sequence" or a "protein-coding sequence" is a polynucleotide sequence capable of being transcribed into mRNA and/or capable of being translated into a polypeptide. The boundaries of the coding sequence are typically determined by a translation start codon at the 5'-terminus and a translation stop codon at the 3'-terminus.

4. A "complement" of a nucleic acid sequence refers to the "antisense" sequence that participates in Watson-Crick base-pairing with the original sequence.

5. An "isolated" nucleic acid or polypeptide refers to component that is removed from its original environment (for example, its natural environment if it is naturally occurring). An isolated nucleic acid or polypeptide preferably contains less than about 50%, more preferably less than about 75%, and most preferably less than about 90%, of the cellular components with which it was originally associated.

6. A nucleic acid or polypeptide sequence that is "derived from" a designated sequence refers to a sequence that corresponds to a region of the designated sequence. For nucleic acid sequences, this encompasses sequences that are homologous or complementary to the sequence, as well as "sequence-conservative variants" and "function-conservative variants." For polypeptide sequences, this encompasses "function-conservative variants." Sequence-conservative variants are those in which a change of one or more nucleotides in a given codon position results in no alteration in the amino acid encoded at that position. Function-conservative variants are those in which a given amino acid residue in a polypeptide has been changed without substantially altering the overall conformation and function of the native polypeptide, including, but not limited to, replacement of an amino acid with one having similar physico-chemical properties (such as, for example, acidic, basic, hydrophobic, and the like). "Function-conservative" variants also include any polypeptides that have the ability to elicit antibodies specific to a designated polypeptide.

7. A "probe" refers to a nucleic acid or oligonucleotide that forms a hybrid structure with a sequence in a target region due to complementarity of at least one sequence in the probe with a sequence in the target.

8. Nucleic acids are "hybridizable" to each other when at least one strand of nucleic acid can anneal to another nucleic acid strand under defined stringency conditions. Stringency of hybridization is determined, e.g., by a) the temperature at which hybridization and/or washing is performed, and b) the ionic strength and polarity (e.g., formamide) of the hybridization and washing solutions, as well as other parameters. Hybridization requires that the two nucleic acids contain substantially complementary sequences; depending on the stringency of hybridization, however, mismatches may be tolerated. The appropriate stringency for hybridizing nucleic acids depends on the length of the nucleic acids and the degree of complementarity, variables well known in the art.

9. An "immunogenic component" is a moiety that is capable of eliciting a humoral and/or cellular immune response in a host animal.

10. An "antigenic component" is a moiety that binds to its specific antibody with sufficiently high affinity to form a detectable antigen-antibody complex.

11. A "sample" refers to a biological sample, such as, for example, tissue or fluid isolated from an individual or from an in vitro cell culture constituents, as well as samples obtained from laboratory procedures.

The invention provides nucleic acid sequences encoding mammalian proteins expressed on monocytes. While specific human monocyte-derived genes and gene products are described herein, the invention encompasses structurally (e.g., sequence) related embodiments from other sources or mammalian species, including polymorphic or individual variants. These will include, e.g., proteins which exhibit relatively few changes in sequence, e.g., less than about 5%, and number, e.g., less than 20 residue substitutions, typically less than 15, preferably less than 10, and more preferably less than 5 substitutions. These will also include versions which are truncated from full length and fusion proteins containing substantial segments of these sequences.

A gene/gene product, isolated from human monocyte cell library and designated FDF03, has been previously described in published International application WO 98/24906, the disclosure of which is incorporated herein in its entirety by reference. The FDF03 gene encodes a type I transmembrane protein comprising an extracellular portion characterized by Ig-like domains, indicating that this gene encodes a receptor member of the Ig superfamily.

SEQ NO: 1 shows the nucleic acid sequence encoding human FDF03 protein. The amino acid sequence of the FDF03 protein is shown in SEQ ID NO: 2. The putative coding region runs from about nucleotide 154 to nucleotide 1062. An N-terminal hydrophobic sequence corresponding to a putaive signal sequence runs from about amino acid residue −19 (Met) to amino acid residue −1 (Leu). An internal hydrophobic sequence corresponding to a putative transmembrane segment runs from about residue 177 (Ala) to residue 199 (Leu). The extracellular region is about 170 amino acids, with a potential Ig-like domain structure. The intracellular region is about 80 residues. Sequence analysis indicates similarity to GenBank clones H26010 and R50327 from humans.

Four human FDF03 homologs have now been discovered.

FDF03-ΔTM

The second human clone, designated FDF03-deltaTM (FDF03-ΔTM), appears to be a soluble form of human FDF03 generated by alternative splicing. The nucleic acid sequence encoding FDF03-ΔTM is shown in SEQ NO: 3. The amino acid sequence of the FDF03-ΔTM protein is shown in SEQ ID NO: 4.

cDNA of the FDF03-ΔTM molecule was amplified along with that of FDF03 during the analysis of human FDF03 expression by RT-PCR. Using primers designed in the 5'-UTR and 3'-UTR of FDF03 gene (FDF03-U25: 5'-ACAGCCCTCTTCGGAGCCTCA (SEQ ID NO: 11) and FDF03-L1166: 5'-AAGCTGGCCCTGAACTCCTGG (SEQ ID NO: 12)), an approximately 200 base pair shorter band was amplified by RT-PCR from PMA/ionomycin activated PBL cDNA, then gel purified, cloned and sequenced. Different clones contained an identical insert of 943 base pairs with an open reading frame encoding a type I protein of 230 amino acids. The deduced amino acid sequence of FDF03-ΔTM matched perfectly with that of FDF03, but contained a gap of 73 amino acids that deleted the extracellular threonine-rich region and the transmembrane domain of FDF03. This resulted in a protein with a potential hydrophobic signal peptide followed by the extracellular Ig like-domain linked to the intracytoplasmic domain of FDF03. cDNA alignments with FDF03 sequence identified a deletion of 219 nucleotides in the FDF03-ΔTM sequence (FDF03 nucleotide 608 to 827) that did not introduce premature stop codons, suggesting that this molecule is the product of an alternative splicing. This molecule is believed to be a secreted soluble form of FDF03 and believed to bind to the same ligand(s) as FDF03.

The protein alignment of the FDF03 (SEQ ID NO: 2) and FDF03-ΔTM (SEQ ID NO: 4) is shown below.

```
  1 MGRPLLLPLLPLLLPPAFLQPSGSTGSGPSYLYGVTQPKHLSASMGGSVEIPFSFYYPWE     FDF03
  1 MGRPLLLPLLPLLLPPAFLQPSGSTGSGPSYLYGVTQPKHLSASMGGSVEIPFSFYYPWE     FDF03-ΔTM

61 LATAPDVRISWRRGHFHGQSFYSTRPPSIHKDYVNRLFLNWTEGQKSGFLRISNLQKQDQ     FDF03
 61 LATAPDVRISWRRGHFHGQSFYSTRPPSIHKDYVNRLFLNWTEGQKSGFLRISNLQKQDQ     FDF03-ΔTM

121 SVYFCRVELDTRSSGRQQWQSIEGTKLSITQAVTTTTQRPSSMTTTWRLSSTTTTTGLRV     FDF03
121 SVYFCRVELDTRSSGRQQWQSIEGTKLSITQ---------------------------     FDF03-ΔTM

181 TQGKRRSDSWHISLETAVGVAVAVTVLGIMILGLICLLRWRRRKGQQRTKATTPAREPFQ     FDF03
152 ------------------------------------------GQQRTKATTPAREPFQ     FDF03-ΔTM

241 NTEEPYENIRNEGQNTDPKLNPKDDGIVYASLALSSSTSPRAPPSHRPLKSPQNETLYSV     FDF03
168 NTEEPYENIRNEGQNTDPKLNPKDDGIVYASLALSSSTSPRAPPSHRPLKSPQNETLYSV     FDF03-ΔTM

303 LKA                                                             FDF03
230 LKA                                                             FDF03-ΔTM
(- : deletion)
```

FDF03-S1

The third clone, designated FDF03-Short1 (FDF03-S1), is an Ig-like molecule homologous to FDF03 but with a short intracytoplasmic domain and a charged residue in transmembrane domain. Comparative DNA and protein analysis suggests the presence of different genes for FDF03 and FDF03S1, rather than alternatively spliced products. The nucleic acid sequence encoding FDF03-S1 is shown in SEQ NO: 5. The amino acid sequence of the FDF03-S1 protein is shown in SEQ ID NO: 6.

FDF03-S1 is a type I transmembrane protein belonging to the Ig superfamily. FDF03-S1 contains a hydrophobic leader sequence followed by an extracellular region (~170 residues) with a V-type Ig domain structure homologous to that of FDF03 (88% homology at the amino acid level). Unlike FDF03, FDF03-S1 possesses a transmembrane domain with a charged amino acid (K), and a small intracellular tail (15 residues) without ITIM or internalization motif. FDF03-S1 is believed to represent an activation isoform of FDF03 and may associate with ITIM-bearing molecules such as DAP12. The amino acid sequence is shown below, wherein the signal peptide and transmembrane domain are underlined. The charged amino acid, lysine (K), residue (arrow) in the transmembrane domain may permit association with another chain, for example DAP12.

```
                                                            (SEQ ID NO: 6)
MGRPLLLPLLLLLQPPAFLQPGGSTGSGPSYLYGVTQPKHLSASMGGSVEIPFSFYYPWEL

AIVPNVRISWRRGHFHGQSFYSTRPPSI-
HKDYVNRLFLNWTEGQESGFLRISNLRKEDQSV

YFCRVELDTRRSGRQQLQSIKGT-
KLTITQAVTTTTTWRPSSTTTIAGLRVTESKGHSESWH

LSLDTAIRVALAVAVLKTVILGLLCLLLLWWRRRKGSRAPSSDF
                 ↑

The protein alignment of FDF03 (SEQ ID NO: 2) and FDF03-S1
(SEQ ID NO: 6) is shown below.

1 MGRPLLLPLLPLLLPPAFLQPSGSTGSGPSYLYGVTQPKHLSASMGGSVEIPFSFYYPWE     FDF03
  1 MGRPLLLPLLLLLQPPAFLQPGGSTGSGPSYLYGVTQPKHLSASMGGSVEIPFSFYYPWE     FDF03-S1
           +  +       +

61 LATAPDVRISWRRGHFHGQSFYSTRPPSIHKDYVNRLFLNWTEGQKSGFLRISNLQKQDQ     FDF03
 61 LAIVPNVRISWRRGHFHGQSFYSTRPPSIHKDYVNRLFLNWTEGQESGFLRISNLRKEDQ     FDF03-S1
      ++ +                                         +           +  + +

121 SVYFCRVELDTRSSGRQQWQSIEGTKLSITQAVTTTTQRPSSMTTTWRLSSTTTTTGLRV     FDF03
121 SVYFCRVELDTRRSGRQQLQSIKGTKLTITQAVTTTT........TWRPSSTTTIAGLRV     FDF03-S1
                +       +   +   +          ++++++++    +       ++

181 TQGKRRSDSWHISLETAVGVAVAVTVLGIMILGLICLL..RWRRRKGQQRTKATTPAREP     FDF03
173 TESKGHSESWHLSLDTAIRVALAVAVLKTVILGLLCLLLLWWRRRKGSRAPSSDF          FDF03-S1
     ++ ++ +     +    +  +  ++ +  +   +++       +      +++     ++++++++

239 FQNTEEPYENIRNEGQNTDPKLNPKDDGIVYASLALSSSTSPRAPPSHRPLKSPQNETLY     FDF03

299 SVLKA                                                           FDF03
+ : residue different or gap
```

Distribution studies (RT-PCR) shows strong expression in B cells (pool resting+activated), T cells and PBL. Lower expression was observed in monocytes, dendritic cells and granulocytes.

FDF03-M14

The fourth clone, designated FDF03-M14, is a potential soluble form of human FDF03 generated by alternative splicing. The nucleic acid sequence encoding FDF03-M14 is shown in SEQ ID NO: 7. The amino acid sequence of the FDF03-M14 protein is shown in SEQ ID NO: 8. cDNA of this molecule was amplified along with that of FDF03 during the analysis of human FDF03 expression by RT-PCR. Using primers designed in the 5'-UTR and 3'-UTR of FDF03 gene (FDF03-U25: 5'-ACAGCCCTCTTCGGAGCCTCA (SEQ ID NO: 11) and FDF03-L1166: 5'-AGCTGGCCCT-GAACTCCTGG (SEQ ID NO: 12)), an approximately 200 base pair shorter band was amplified by RT-PCR from activated PBL cDNA, then gel purified, cloned and sequenced. One clone (M14) contained an insert of 908 base pairs with an ORF encoding a type I protein of 175 amino acids. cDNA alignments with FDF03 sequence identified a deletion of 253 nucleotides in FDF03-M14 sequence (FDF03 nucleotide 608 to 861) that deleted the sequences encoding the extracellular threonine-rich region, the transmembrane domain and the start of the intracytoplasmic domain of FDF03, and that introduced a premature stop codon at position 655 of FDF03-M14. The deduced amino acid sequence of FDF03-M14 resulted in a protein with a potential hydrophobic signal peptide followed by an extracellular Ig like-domain that matched perfectly with that of FDF03, but that was linked to a COOH-terminal 24 amino acid sequence different from FDF03. This molecule may be the product of an alternative splicing of FDF03 mRNA.

Like FDF03-ΔTM, this molecule may represent a secreted soluble form of FDF03 and may bind to the same ligand(s) as FDF03. The amino acid sequence is shown below, wherein the signal sequence is underlined.

MGRPLLLPLLPLLLPPAFLQPSGSTGSGPSYLYGVT
QPKHLSASMGGSVEIPFSFYYPWELATAPDVRIS
WRRGHFHGQSFYSTRPPSIHKDYVNRLFLNWTE
GQKSGFLRISNLQKQDQSVYFCRVELDTRSSGR
QQWQSIEGTKLSITQGNPSKTQRSHMRISGMR
DKIQIPS (SEQ ID NO: 8)

The protein alignment of FDF03 (SEQ ID NO: 2) and FDF03-M14 (SEQ ID NO: 8) is shown below.

This molecule is highly homologous to FDF03-S1 and is a potential DAP12-associated protein. The nucleic acid sequence encoding FDF03-S2 is shown is SEQ ID NO: 9. The amino acid sequence of the FDF03-S2 protein is shown in SEQ ID NO: 10.

cDNA of this molecule was amplified using primers specific for FDF03-S2. Specificity is obtained with forward primer designed in 5'UTR of FDF03-S2. FDF03-S2-forward: 5'-CAAGG-GATAAAAAGGCAC (SEQ ID NO: 13) (does not amplify FDF03, FDF03ΔTM or FDF03-S1). FDF03-S2-reverse: 5'-AACTCTCCTCCAGTCGGT (SEQ ID NO: 14) (can amplify FDF03-S1, but not FDF03 or FDF03deltaTM).

FDF03-S2 is a type I transmembrane protein belonging to the Ig superfamily. FDF03-S2 contains a hydrophobic leader sequence followed by an extracellular region (~170 residues) with one V-type Ig domain structure homologous to that of FDF03 (~85% homology at the amino acid level). Unlike FDF03, FDF03-S2 possesses a transmembrane domain with a charged amino acid (K), and a small intracellular tail (15 residues) without ITIM or internalization motif. FDF03-S2 is highly homologous to FDF03-S1 (3 amino acid difference in the extracellular domain and one amino acid missing in the transmembrane domain). Like FDF03-S1, FDF03-S2 may represent an activation isoform of FDF03 and may associate with ITAM-bearing molecules such as DAP12.

There are two putative start codons in frame (position 117 and 309). The first one is not contained within a typical Kozak sequence. The sequence shown below is deduced from the second start codon (nucleotide 309), as starting at the first start codon in frame (position 117) does not encode for a hydrophobic sequence followed by another Ig-like domain.

```
  1 MGRPLLLPLLPLLLPPAFLQPSGSTGSGPSYLYGVTQPKHLSASMGGSVEIPFSFYYPWE    FDF03
  1 MGRPLLLPLLPLLLPPAFLQPSGSTGSGPSYLYGVTQPKHLSASMGGSVEIPFSFYYPWE    FDF03-14

61 LATAPDVRISWRRGHFHGQSFYSTRPPSIHKDYVNRLFLNWTEGQKSGFLRISNLQKQDQ    FDF03
 61 LATAPDVRISWRRGHFHGQSFYSTRPPSIHKDYVNRLFLNWTEGQKSGFLRISNLQKQDQ    FDF03-M14

121 SVYFCRVELDTRSSGRQQWQSIEGTKLSITQAVTTTTQRPSSMTTTWRLSSTTTTTGLRV    FDF03
121 SVYFCRVELDTRSSGRQQWQSIEGTKLSITQGNPSKTQRSHMRISGMRDKIQIPS         FDF03-M14
                                   *****  ******* *******

181 TQGKRRSDSWHISLETAVGVAVAVTVLGIMILGLICLLRWRRRKGQQRTKATTPAREPFQ    FDF03

241 NTEEPYENIRNEGQNTDPKLNPKDDGIVYASLALSSSTSPRAPPSHRPLKSPQNETLYSVLKA FDF03
*: residue different
```

FDF03-S2

The fifth clone, designated FDF03-S2 is an Ig-like molecule homologous to FDF03 but with a short intracytoplasmic domain and a charged residue in transmembrane domain.

In the sequence shown below, the signal peptide and transmembrane domain are underlined. The charged amino acid, lysine (K) residue (arrow) in transmembrane domain may permit association with another chain, for example DAP12.

<u>MGRPLLLPLLLLL QPPA</u>FLQPGGSTGSGPSYLYGVTQPKHLSASMGGSVEIPFSFYYPWE

LATAPDVRISWRRGHFHGQSFYSTRPPSIHKDYVNRLFLNWTEGQESGFLRISNLRKEDQ

SVYFCRVELDTRRSGRQQLQSIKGTKLTITQAVTTTTTWRPSSTTTIAGLRVTESKGHSE

SWHLSLDTAIR<u>VALAVAVLKTVILGLLCLLL</u>WWRRRKGSRAPSSDF
           ↑

The protein alignments of FDF03, FDF03-S1 and FDF03-S2 is shown below.

```
1 MGRPLLLPLLPLLLPPAFLQPSGSTGSGPSYLYGVTQPKHLSASMGGSVEIPFSFYYPWE FDF03
1 MGRPLLLPLLLLLQPPAFLQPGGSTGSGPSYLYGVTQPKHLSASMGGSVEIPFSFYYPWE FDF03-S1
1 MGRPLLLPLLLLLQPPAFLQPGGSTGSGPSYLYGVTQPKHLSASMGGSVEIPFSFYYPWE FDF03-S2
          +  +        +
```

```
 61 LATAPDVRISWRRGHFHGQSFYSTRPPSIHKDYVNRLFLNWTEGQKSGFLRISNLQKDQ FDF03
 61 LAIVPNVRISWRRGHFHGQSFYSTRPPSIHKDYVNRLFLNWTEGQESGFLRISNLRKEDQ FDF03-S1
 61 LATAPDVRISWRRGHFHGQSFYSTRPPSIHKDYVNRLFLNWTEGQESGFLRISNLRKEDQ FDF03-S2
** *                                              +         + +

121 SVYFCRVELDTRSSGRQQWQSIEGTKLSITQAVTTTTQRPSSMTTTWRLSSTTTTTGLRV FDF03
121 SVYFCRVELDTRRSGRQQLQSIKGTKLTITQAVTTTT........TWRPSSTTTIAGLRV FDF03-S1
121 SVYFCRVELDTRRSGRQQLQSIKGTKLTITQAVTTTT........TWRPSSTTTIAGLRV FDF03-S2
            +    + +  +            ++++++++   +     ++

181 TQGKRRSDSWHISLETAVGVAVAVTVLGIMILGLICLL..RWRRRKGQQRTKATTPAREP FDF03
173 TESKGHSESWHLSLDTAIRVALAVAVLKTVILGLLCLLLLWWRRRKGSRAPSSDF      FDF03-S1
173 TESKGHSESWHLSLDTAIRVALAVAVLKTVILGLLCLLL.WWRRRKGSRAPSSDF      FDF03-S2
     ++ ++ +    +  +   ++   +   +  +++    +   +*+      ++++++++

239 FQNTEEPYENIRNEGQNTDPKLNPKDDGIVYASLALSSSTSPRAPPSHRPLKSPQNETLY FDF03

299 SVLKA                                                        FDF03
+ : residue different or gap between FDF03-S2/FDF03-S1 and FDF03
* : residue different or gap between FDF03-S2/FDF03 and FDF03-S1
```

Distribution studies (RT-PCR) shows expression in activated dendritic cells (CD34-derived), PBMC, monocytes and tonsil B cells.

Alignment with human IgV domains (SEQ ID NO: 15) and TCR V domain (SEQ ID NO: 16) is given below. This alignment shows the conserved VDJ structure of FDF03.

The localization of the genes encoding FDF03 (including the ΔTM and M14 forms) and FDF03-S1 on human chromosome 7q22 is interesting because this region is frequently deleted in myelodystrophic syndromes such as Acute Myeloid Leukemia (AML). The implication of the possible deletion of a myeloid inhibitory receptor in a proliferative disease leads to a possible use in gene therapy.

```
Ig V region  QVQ.LQESGPG.LVKPSETLSLTCTVSGGSVSSGSYYWSW.IRQAPGKGLEWIG
TCR human    QVQ.LQESGPG.LVKPSETLSLTCTVSGSYSISSG.YYWGW.IRQPPGKGLEWIG
FDF03        QPSGSTGSGPSYLYGVTQPKHLSASMGGSVEIPFSFYYPWELATAPDVRISWRR
FDF03-S1      QPGGSTGSGPSYLYGVTQPKHLSASMGGSVEIPFSFYYPWELAIVPNVRISWRR
FDF03-S2      QPGGSTGSGPSYLYGVTQPKHLSASMGGSVEIPFSFYYPWELATAPDVRISWRR
                +   +++   +       +       +  +    +       +

Ig V region  YIYYSGSTNY.......NRSHKSRVNIS.VDTAKNQFSLKLSSVSTADTAVYYCARIT
TCR human    SIYHSGSTYY.......NPSLKSRVTIS.VDTSKNQFSLKLSSVTAADTAVYYCARVR
FDF03        GHFH.GQSFYSTRPPSIHKDYVNRLFLNWTEGQKSGF.LRISNLQKQDQSVYFC.RVE
FDF03-S1     GHFH.GQSFYSTRPPSIHKDYVNRLFLNWTEGQESGF.LRISNLRKEDQSVYFC.RVE
FDF03-S2     GHFH.GQSFYSTRPPSIHKDYVNRLFLNWTEGQESGF.LRISNLRKEDQSVYFC.RVE
                +    +            +         + +     +   + ++ + +

Ig V region  TTVPSSWYYYYMDVWDKGTTVTVSS
TCR human    RRYSSSAS...KIIFGSGTRLSIR.
FDF03        LDTRSSGRQQWQS..IEGTKLSITQ
FDF03-S1      LDTRRSGRQQLQS..IKGTKLTITQ
FDF03-S2      LDTRRSGRQQLQS..IKGTKLTITQ
                 +                ++
```

Studies of human genomic DNA clones show that chromosome 7 contains both FDF03-S1 and FDF03 specific sequences, confirming that the two molecules are encoded by two different genes. These studies also suggest that FDF03-S1 and -S2 genes are two different alleles of the same gene. In addition, PCR from intronic sequence surrounding the areas of difference between S1 and S2 on genomic DNA from different donors shows the existence of homozygotes and S1/S2 heterozygotes at this locus. It is thus likely that these two cDNAs are from different alleles.

The genomic organization of the FDF03 gene confirms that FDF03-ΔTM is produced by alternative splicing (deletion of exon 3 coding for the hinge region and TM domain). This is also the case for FDF03-M14 (deletion of exons 3 and 4).

The two forms of FDF03-S1/2 may be advantageously used as population markers. The two forms of this protein will either not bind the same ligand (e.g., as in the case of the NK receptor family) or will bind at different affinities, thus potentially giving individuals a different response to receptor/ligand interaction.

Nucleic Acids, Vectors, and Host Cells

The invention provides nucleic acid sequences, in particular the nucleic acid sequences shown in SEQ ID NO: 1, 5, 7 or 9 or nucleic acid sequences which encode an amino acid sequences shown in SEQ ID NO: 2, 4, 6, 8 or 10. The invention encompasses isolated nucleic acid fragments comprising all or part of the individual nucleic acid sequences disclosed herein. The nucleic acid sequences of the invention comprise at least about 12, preferably at least about 18, more preferably at least about 20-35 and most preferably at least about 35-55 or more consecutive nucleotides, including complete protein-coding sequences, or complements thereof. The invention encompasses sequence-conservative variants and function-conservative variants of these sequences.

Nucleic acids comprising any of the sequences disclosed herein or subsequences thereof can be prepared by standard methods using the nucleic acid sequence information provided in SEQ ID NO: 1, 3, 5, 7 and 9. For example, nucleic acids can be chemically synthesized using, e.g., the phosphoramidite solid support method of Matteucci et al., 1981, *J. Am. Chem. Soc.* 103:3185, the method of Yoo et al., 1989, *J. Biol. Chem.* 764:17078, or other well known methods. This can be done by sequentially linking a series of oligonucleotide cassettes comprising pairs of synthetic oligonucleotides. The nucleic acids may be isolated directly from cells. Alternatively, the polymerase chain reaction (PCR) method can be used to produce the nucleic acids of the invention, using either chemically synthesized strands or genomic material as templates. Primers used for PCR can be synthesized using the sequence information provided herein and can further be designed to introduce appropriate new restriction sites, if desirable, to facilitate incorporation into a given vector for recombinant expression. Of course, due to the degeneracy of the genetic code, many different nucleotide sequences can encode polypeptides having the amino acid sequences defined by SEQ ID NO: 2, 4, 6, 8 or 10 subsequences thereof. The codons can be selected for optimal expression in prokaryotic or eukaryotic systems. Such degenerate variants are also encompassed by this invention.

The encoded polypeptides may be expressed by using many known vectors such as pUC plasmids, pET plasmids (Novagen, Inc., Madison, Wis.), or pRSET or pREP (Invitrogen, San Diego, Calif.), and many appropriate host cells such as *Escherichia coli, Saccharomyces cerevisiae*, and insect and mammalian cell lines using methods known to those skilled in the art. The particular choice of vector/host is not critical to the practice of the invention.

The nucleic acids of the present invention find use, e.g., as templates for the recombinant production of peptides or polypeptides, as probes and primers for the detection of the human genes described herein, for chromosome mapping, and as probes or to design PCR primers to identify homologous genes in other mammalian species. Homology may be determined experimentally. Alternatively, homology analysis may be performed computationally. In practicing the present invention, a gene that shares at least about 70% DNA sequence homology at the nucleotide level with the genome of another mammalian species is considered to be present in that species. The determination that a gene is present in another mammal may be achieved using any technique known in the art. Appropriate techniques include without limitation hybridization to genomic DNA, colony hybridization to a genomic or cDNA library, polymerase chain reaction (PCR) using degenerate primers or gene-specific primers and genomic DNA as a template, genetic complementation, antibody cross-reactivity, or biochemical complementation in vitro.

In applying these techniques, conditions are established that discriminate different levels of homology between probe and template. For example, for hybridization of a probe to immobilized DNA (whether in a Southern blot, dot blot, or colony hybridization format), varying the SSC concentration in the buffer allows the detection of hybrids having different levels of homology (1×SSC is 0.15 M NaCl–0.015 M Na citrate). In a wash buffer containing 6M urea and 0.4% sodium dodecyl sulfate, the presence of 2×SSC, 0.5×SSC, 0.1×SSC, and 0.05×SSC allows the formation of hybrids having threshold homologies of at least 55%+5%, 65%+5%, 75%+5%, and >85%, respectively. Preferably, once a gene has been identified in another organism by hybridization or PCR, the DNA sequence of the gene is determined directly.

It will be understood that some methods that detect homologous sequences may result in the identification or isolation of only a portion of the entire protein-coding sequence of a particular gene. The entire protein-coding sequence can be isolated and identified, for example, by using an isolated nucleic acid encoding the known portion of the sequence, or fragments thereof, to prime a sequencing reaction with cDNA as template; this is followed by sequencing the amplified product. The isolated nucleic acid encoding the disclosed sequence, or fragments thereof, can also be hybridized to appropriate cDNA libraries to identify clones containing additional complete segments of the protein-coding sequence of which the shorter sequence forms a part. Then, the entire protein-coding sequence, or fragments thereof, or nucleic acids encoding all or part of the sequence, or sequence-conservative or function-conservative variants thereof, may be employed in practicing the present invention.

In a similar manner, additional sequences derived from the 5' and 3' flanking regions of sequence encoding the protein, including regulatory sequences, may be isolated, and the nucleotide sequence determined.

Polypeptides

Both the naturally occurring and recombinant forms of the polypeptides described herein, including both glycosylated and non-glycosylated forms are encompassed by the invention. The polypeptides of the present invention, including function-conservative variants, may be isolated from human monocytes, or from heterologous organisms or cells (e.g., bacteria, fungi, insect, plant, and mammalian cells) into which a protein-coding sequence has been introduced and expressed. The proteins described herein, or portions thereof, also may be expressed as fusions with other proteins. The polypeptides may be chemically synthesized by commercially available automated procedures, including, without limitation, exclusive solid phase synthesis, partial solid phase methods, fragment condensation or classical solution synthesis. The polypeptides can also, advantageously, be made by in vitro translation.

Methods for polypeptide purification are well-known in the art, including, without limitation, preparative disc-gel electrophoresis, isoelectric focusing, sucrose density gradient centrifugation, HPLC, reversed-phase HPLC, gel filtration, ion exchange and partition chromatography, and countercurrent distribution. For some purposes, it is preferable to produce the polypeptide in a recombinant system in which the protein contains an additional sequence tag that facilitates purification, such as, but not limited to, a polyhistidine sequence. The polypeptide can then be purified from a crude lysate of the host cell by chromatography on an appropriate solid-phase matrix. Alternatively, antibodies produced against a protein or against peptides derived therefrom can be used as purification reagents. Other purification methods are possible.

The present invention also encompasses derivatives and homologues of the polypeptides specifically disclosed herein. For some purposes, nucleic acid sequences encoding the peptides may be altered by substitutions, additions, or deletions that provide for functionally equivalent molecules, i.e., function-conservative variants. For example, one or more amino acid residues within the sequence can be substituted by another amino acid of similar properties, such as, for example, positively charged amino acids (arginine, lysine, and histidine); negatively charged amino acids (aspartate and glutamate); polar neutral amino acids; and non-polar amino acids.

The isolated polypeptides may be modified by, for example, phosphorylation, sulfation, acylation, or other protein modifications. They may also be modified with a label capable of providing a detectable signal, either directly or indirectly, including, but not limited to, radioisotopes and fluorescent compounds.

The polypeptides of the invention find use, e.g., for binding studies, for construction and expression of modified molecules, for structure/function studies and for the preparation of polyclonal and monoclonal antibodies. Polypeptides useful as immunogenic components for preparing antibodies or as targets for binding agent studies are at least five or more residues in length. Preferably, the polypeptides comprise at least about 12, more preferably at least about 20, and most preferably at least about 30 or more residues. Methods for obtaining these polypeptides are well known and are explained in *Immunochemical Methods in Cell and Molecular Biology*, 1987 (Mayer and Waler, eds; Academic Press, London); Scopes, 1987, *Protein Purification: Principles and Practice*, Second Edition (Springer-Verlag, N.Y.) and *Handbook of Experimental Immunology*, 1986, Volumes I-IV (Weir and Blackwell, eds.).

Having isolated one member of a binding partner of a specific interaction, methods exist for isolating the counterpartner. See, e.g., Gearing et al., 1989, *EMBO J.* 8:3667-3676. Many methods of screening for binding activity are known by those skilled in the art and may be used to practice the invention. For example, an expression library can be screened for specific binding to the protein, e.g., by cell sorting, or other screening to detect subpopulations which express such a binding component. See, e.g., Ho et al., 1993, *Proc. Natl. Acad Sci. USA* 90:11267-11271. Alternatively, a panning method may be used. See, e.g., Seed and Aruffo, 1987, *Proc. Natl. Acad. Sci. USA* 84:3365-3369. A two-hybrid selection system may also be applied making appropriate constructs with the available protein sequences. See, e.g., Fields and Song, 1989, *Nature* 340:245-246. Several methods of automated assays have been developed in recent years so as to permit screening of tens of thousands of compounds in a short period of time.

Physical Variants

This invention also encompasses proteins or peptides having substantial amino acid sequence similarity with an amino acid sequence of a SEQ ID NO: 2, 4, 6, 8 or 10. Variants exhibiting substitutions, e.g., 20 or fewer, preferably 10 or fewer, and more preferably 5 or fewer substitutions, are encompassed. Where the substitutions are conservative substitutions, the variants will share immunogenic or antigenic similarity or cross-reactivity with a corresponding natural sequence protein. Natural variants include individual, allelic, polymorphic, strain, or species variants.

Amino acid sequence similarity, or sequence identity, is determined by optimizing residue matches, if necessary, by introducing gaps as required. This changes when considering conservative substitutions as matches. Conservative substitutions typically include substitutions within the following groups: glycine, alanine; valine, isoleucine, leucine; aspartic acid, glutamic acid; asparagine, glutamine; serine, threonine; lysine, arginine; and phenylalanine, tyrosine. Homologous amino acid sequences include natural allelic and interspecies variations in each respective protein sequence. Typical homologous proteins or peptides will have from 50-100% similarity (if gaps can be introduced), to 75-100% similarity (if conservative substitutions are included) with the amino acid sequence of the relevant protein. Identity measures will be at least about 50%, generally at least 60%, more generally at least 65%, usually at least 70%, more usually at least 75%, preferably at least 80%, and more preferably at least 80%, and in particularly preferred embodiments, at least 85% or more. See also Needleham et al., 1970, *J. Mol. Biol.* 48:443-453; Sankoff et al., 1983, *Time Warps, String Edits, and Macromolecules: The Theory and Practice of Sequence Comparison* Chapter One, Addison-Wesley, Reading, Mass.; and software packages from IntelliGenetics, Mountain View, Calif.; and the University of Wisconsin Genetics Computer Group (GCG), Madison, Wis.

Nucleic acids encoding the corresponding proteins will typically hybridize to SEQ ID NO: 1, 3, 5, 7 or 9 under stringent conditions. For example, nucleic acids encoding the respective proteins will typically hybridize to the nucleic acid of SEQ ID NO: 1, 3, 5, 7 or 9 under stringent hybridization conditions, while providing few false positive hybridization signals. Generally, stringent conditions are selected to be about 10° C. lower than the thermal melting point (Tm) for the sequence being hybridized to at a defined ionic strength and pH. The Tm is the temperature (under defined ionic strength and pH) at which 50% of the target sequence hybridizes to a perfectly matched probe. Typically, stringent conditions will be those in which the salt concentration in wash is about 0.02 molar at pH 7 and the temperature is at least about 50° C. Other factors may significantly affect the stringency of hybridization, including, among others, base composition and size of the complementary strands, the presence of organic solvents such as formamide, and the extent of base mismatching. A preferred embodiment will include nucleic acids that will bind to disclosed sequences in 50% formamide and 20-50 mM NaCl at 42° C.

An isolated nucleic acid can be readily modified by nucleotide substitutions, nucleotide deletions, nucleotide insertions, and inversions of nucleotide stretches. These modifications result in novel DNA sequences which encode these antigens, their derivatives, or proteins having highly similar physiological, immunogenic, or antigenic activity.

Modified sequences can be used to produce mutant antigens or to enhance expression. Enhanced expression may involve gene amplification, increased transcription, increased translation, and other mechanisms. Such mutant protein derivatives include predetermined or site-specific mutations of the respective protein or its fragments. "Mutant protein" encompasses a polypeptide otherwise falling within the homology definition of the proteins as set forth above, but having an amino acid sequence which differs from that of the protein as found in nature, whether by way of deletion, substitution, or insertion. In particular, "site specific mutant protein" generally includes proteins having significant similarity with a protein having a sequence of SEQ ID NO: 2, 4, 6, 8 or 10. Generally, the variant will share many physicochemical and biological activities, e.g., antigenic or immunogenic, with those sequences, and in preferred embodiments contain most or all of the disclosed sequence.

Glycosylation alterations are included, e.g., made by modifying the glycosylation patterns of a polypeptide during its synthesis and processing, or in further processing steps. Particularly preferred means for accomplishing this are by exposing the polypeptide to glycosylating enzymes derived from cells that normally provide such processing, e.g., mammalian glycosylation enzymes. Deglycosylation enzymes are also contemplated. Also embraced are versions of the same primary amino acid sequence which have other minor modifications, including phosphorylated amino acid residues, e.g., phosphotyrosine, phosphoserine, or phosphothreonine, or other moieties, including ribosyl groups or cross-linking reagents. Also, proteins comprising substitutions are encompassed, which should retain substantial immunogenicity, to produce antibodies that recognize a protein of SEQ ID NO: 2, 4, 6, 8 or 10. Typically, these proteins will contain less than 20 residue substitutions from the disclosed sequence, more typically less than 10 substitutions, preferably less than 5, and more preferably less than three. Alternatively, proteins that begin and end at structural domains will usually retain antigenicity and cross immunogenicity.

A major group of derivatives are covalent conjugates of the proteins described herein or fragments thereof with other proteins or polypeptides. These derivatives can be synthesized in recombinant culture such as N- or C-terminal fusions or by the use of agents known in the art for their usefulness in cross-linking proteins through reactive side groups. Preferred protein derivatization sites with cross-linking agents are at free amino groups, carbohydrate moieties, and cysteine residues.

Fusion polypeptides between these proteins and other homologous or heterologous proteins are also provided. Heterologous polypeptides may be fusions between different surface markers, resulting in, e.g., a hybrid protein. Likewise, heterologous fusions may be constructed which would exhibit a combination of properties or activities of the derivative proteins. Typical examples are fusions of a reporter polypeptide, e.g., luciferase, with a segment or domain of a protein, e.g., a receptor-binding segment, so that the presence or location of the fused protein may be easily determined. See, e.g., U.S. Pat. No. 4,859,609. Other gene fusion partners include bacterial β-galactosidase, trpE, Protein A, β-lactamase, alpha amylase, alcohol dehydrogenase, and yeast alpha mating factor. See, e.g., Godowski et al., 1988, *Science* 241: 812-816.

Such polypeptides may also have amino acid residues that have been chemically modified by phosphorylation, sulfonation, biotinylation, or the addition or removal of other moieties, particularly those that have molecular shapes similar to phosphate groups. In some embodiments, the modifications will be useful labeling reagents, or serve as purification targets, e.g., affinity ligands.

This invention also contemplates the use of derivatives of these proteins other than variations in amino acid sequence or glycosylation. Such derivatives may involve covalent or aggregative association with chemical moieties. These derivatives generally fall into the three classes: (1) salts, (2) side chain and terminal residue covalent modifications, and (3) adsorption complexes, for example with cell membranes. Such covalent or aggregative derivatives are useful as immunogens, as reagents in immunoassays, or in purification methods such as for affinity purification of ligands or other binding ligands. For example, a protein antigen can be immobilized by covalent bonding to a solid support such as cyanogen bromide-activated Sepharose, by methods which are well known in the art, or adsorbed onto polyolefin surfaces, with or without glutaraldehyde cross-linking, for use in the assay or purification of antibodies. The proteins can also be labeled with a detectable group, e.g., radioiodinated by the chloramine T procedure, covalently bound to rare earth chelates, or conjugated to another fluorescent moiety for use in diagnostic assays. Purification of these proteins may be accomplished by immobilized antibodies.

Antibodies

The immunogenic components of this invention, as described above, are useful as antigens for preparing antibodies by standard methods. Such immunogenic components can be produced by proteolytic cleavage of larger polypeptides or by chemical synthesis or recombinant technology and are thus not limited by proteolytic cleavage sites. Preferably, smaller immunogenic components will first be rendered more immunogenic by cross-linking or by coupling to an immunogenic carrier molecule (i.e., a macromolecule having the property of independently eliciting an immunological response in a host animal, to which the immunogenic components of the invention can be covalently linked). Cross-linking or conjugation to a carrier molecule may be required because small polypeptide fragments sometimes act as haptens (molecules which are capable of specifically binding to an antibody but incapable of eliciting antibody production, i.e., they are not immunogenic). Conjugation of such fragments to an immunogenic carrier molecule renders them immunogenic through what is commonly known as the "carrier effect".

Antibodies according to the present invention include polyclonal and monoclonal antibodies. The antibodies may be elicited in an animal host by immunization with immunogenic components of the invention or may be formed by in vitro immunization (sensitization) of immune cells. The immunogenic components used to elicit the production of antibodies may be isolated from human cells (e.g., human monocytes) or chemically synthesized. The antibodies may also be produced in recombinant systems programmed with appropriate antibody-encoding DNA. Alternatively, the antibodies may be constructed by biochemical reconstitution of purified heavy and light chains.

The antibodies of this invention can be purified by standard methods, including but not limited to preparative disc-gel electrophoresis, isoelectric focusing, HPLC, reversed-phase HPLC, gel filtration, ion exchange and partition chromatography, and countercurrent distribution. Purification methods for antibodies are disclosed, e.g., in *The Art of Antibody Purification,* 1989, Amicon Division, W.R. Grace & Co. General protein purification methods are described in *Protein Purification: Principles and Practice,* R. K. Scopes, Ed., 1987, Springer-Verlag, New York, N.Y.

Suitable adjuvants for the vaccination of animals include but are not limited to Adjuvant 65 (containing peanut oil, mannide monooleate and aluminum monostearate); Freund's complete or incomplete adjuvant; mineral gels such as aluminum hydroxide, aluminum phosphate and alum; surfactants such as hexadecylamine, octadecylamine, lysolecithin, dimethyldioctadecyl-ammonium bromide, N,N-dioctadecyl-N',N'-bis(2-hydroxymethyl) propane-diamine, methoxyhexadecylglycerol and pluronic polyols; polyanions such as pyran, dextran sulfate, poly IC, polyacrylic acid and carbopol; peptides such as muramyl dipeptide, dimethylglycine and tuftsin; and oil emulsions. The immunogenic components could also be administered following incorporation into liposomes or other microcarriers. Information concerning adjuvants and various aspects of immunoassays are disclosed, e.g., in the series by P. Tijssen, 1987, *Practice and Theory of Enzyme Immunoassays,* 3rd Edition, Elsevier, N.Y.

Serum produced from animals thus immunized can be used directly. Alternatively, the IgG fraction can be separated from the serum using standard methods such as plasmaphoresis or adsorption chromatography using IgG specific adsorbents such as immobilized Protein A.

Hybridomas of the invention used to make monoclonal antibodies against the immunogenic components of the invention are produced by well-known techniques. Usually, the process involves the fusion of an immortalizing cell line with a B-lymphocyte that produces the desired antibody. Alternatively, non-fusion techniques for generating immortal antibody-producing cell lines are possible, and come within the purview of the present invention, e.g., virally-induced transformation, Casali et al., 1986, *Science* 234:476. Immortalizing cell lines are usually transformed mammalian cells, particularly myeloma cells of rodent, bovine, and human origin. Most frequently, rat or mouse myeloma cell lines are employed as a matter of convenience and availability.

Techniques for obtaining the appropriate lymphocytes from mammals injected with the immunogenic components are well known. Generally, peripheral blood lymphocytes (PBLs) are used if cells of human origin are desired, or spleen cells or lymph node cells are used if non-human mammalian sources are desired. A host animal is injected with repeated dosages of a preferably purified immunogenic component, and the animal is permitted to generate the desired antibody-producing cells before these are harvested for fusion with the immortalizing cell line. Techniques for fusion are also well known in the art, and in general involve mixing the cells with a fusing agent, such as polyethylene glycol.

Hybridomas are selected by standard procedures, such as HAT (hypoxanthine-aminopterin-thymidine) selection. From among these hybridomas, those secreting the desired antibody are selected by assaying their culture medium by standard immunoassays, such as Western blotting, ELISA (enzyme-linked immunosorbent assay), RIA (radioimmunoassay), or the like. Antibodies are recovered from the medium using standard protein purification techniques, Tijssen, 1985, *Practice and Theory of Enzyme Immunoassays*, Elsevier, Amsterdam.

Many references are available for guidance in applying any of the above techniques: Kohler et al., 1980, *Hybridoma Techniques*, Cold Spring Harbor Laboratory, New York; Tijssen, 1985, *Practice and Theory of Enzyme Immunoassays*, Elsevier, Amsterdam; Campbell, 1984, *Monoclonal Antibody Technology*, Elsevier, Amsterdam; Hurrell, 1982, *Monoclonal Hybridoma Antibodies: Techniques and Applications*, CRC Press, Boca Raton, Fla. Monoclonal antibodies can also be produced using well known phage library systems.

The use and generation of antibody fragments is also well known, e.g., Fab fragments: Tijssen, 1985, *Practice and Theory of Enzyme Immunoassays*, Elsevier, Amsterdam; Fv fragments: Hochman et al., 1973, *Biochemistry* 12:1130; Sharon et al., 1976, *Biochemistry* 15:1591; Ehrlich et al., U.S. Pat. No. 4,355,023; and antibody half molecules: Auditore-Hargreaves, U.S. Pat. No. 4,470,925. These also may be useful in immunoassays.

These antibodies, whether polyclonal or monoclonal, can be used, e.g., in an immobilized form bound to a solid support by well known methods, to isolate and purify the immunogenic components by immunoaffinity chromatography. The antibodies are useful as probes to distinguish tissue and cell type distribution. The antibodies may be used to screen expression libraries for particular expression products. Usually the antibodies used in such a procedure will be labeled with a moiety allowing easy detection of presence of antigen by antibody binding. Antibodies to proteins may be used for the analysis or, or identification of specific cell population components which express the respective protein. By assaying the expression products of cells expressing the proteins described herein it is possible to diagnose disease, e.g., immune-compromised conditions, monocyte depleted conditions, or overproduction of monocytes. Antibodies raised against the proteins will also be useful to raise anti-idiotypic antibodies. These will be useful in detecting or diagnosing various immunological conditions related to expression of the respective antigens. The present invention encompasses antibodies that specifically recognize monocyte-derived immunogenic components. Such antibodies can be used conventionally, e.g., as reagents for purification of monocyte cell components, or in diagnostic applications.

Diagnostic Applications

The invention encompasses compositions, methods, and kits useful in clinical settings for the qualitative or quantitative diagnosis, i.e., detection of specific components in a biological sample. These applications utilize nucleic acids, peptides/polypeptides, or antibodies specific for the components described herein. Both antibody-based and nucleic acid-based diagnostic methods, including PCR-based diagnostic methods are contemplated. Detection of the level of monocyte cells present in a sample is important for diagnosis of certain aberrant disease conditions. For example, an increase in the number of monocytes in a tissue or the lymph system can be indicative of the presence of a monocyte hyperplasia, tissue or graft rejection, or inflammation. A low monocyte population can indicate an abnormal reaction to, e.g., a bacterial or viral infection, which may require an appropriate treatment to normalize the monocyte response.

Both the naturally occurring and the recombinant form of the proteins of this invention are particularly useful in kits and assay methods which are capable of screening compounds for binding activity to the proteins.

In nucleic-acid-type diagnostic methods, the sample to be analyzed may be contacted directed with the nucleic acid probes. Probes include oligonucleotides at least 12 nucleotides, preferably at least 18, and most preferably 20-35 or more nucleotides in length. Alternatively, the sample may be treated to extract the nucleic acids contained therein. It will be understood that the particular method used to extract DNA will depend on the nature of the biological sample. The resulting nucleic acid from the sample may be subjected to gel electrophoresis or other size separation techniques, or, the nucleic acid sample may be immobilized on an appropriate solid matrix without size separation or used for PCR.

Kits suitable for antibody-based diagnostic applications typically include one or more of the following components:

(i) Antibodies: The antibodies may be pre-labeled; alternatively, the antibody may be unlabelled and the ingredients for labeling may be included in the kit in separate containers, or a secondary, labeled antibody is provided; and (ii) Reaction components: The kit may also contain other suitably packaged reagents and materials needed for the particular immunoassay protocol, including solid-phase matrices, if applicable, and standards.

Kits suitable for nucleic acid-based diagnostic applications typically include the following components:

(i) Probe DNA: The probe DNA may be pre-labeled; alternatively, the probe DNA may be unlabelled and the ingredients for labeling may be included in the kit in separate containers; and (ii) Hybridization reagents: The kit may also contain other suitably packaged reagents and materials needed for the particular hybridization protocol, including solid-phase matrices, if applicable, and standards.

PCR based diagnostic kits are also contemplated and are encompassed by the invention.

The kits referred to above may include instructions for conducting the test. Furthermore, in preferred embodiments, the diagnostic kits are adaptable to high-throughput and/or automated operation.

Therapeutic Applications

The invention also provides reagents that may exhibit significant therapeutic value. The proteins (naturally occurring or recombinant), fragments thereof, and antibodies thereto, along with compounds identified as having binding affinity to the proteins, may be useful in the treatment of conditions associated with abnormal physiology or development. For example, a disease or disorder associated with abnormal expression or abnormal signaling by a monocyte, e.g., as an antigen presenting cell, is a target for an agonist or antagonist of the protein. The proteins likely play a role in regulation or development of hematopoietic cells, e.g., lymphoid cells, which affect immunological responses, e.g., antigen presentation and the resulting effector functions.

Other abnormal developmental conditions are known in cell types shown to possess monocyte protein mRNA by northern blot analysis. See Berkow (ed.) *The Merck Manual of Diagnosis and Therapy*, Merck & Co., Rahway, N.J.; and Thorn, et al. *Harrison's Principles of Internal Medicine*, McGraw-Hill, N.Y. Developmental or functional abnormalities, e.g., of the immune system, cause significant medical abnormalities and conditions that may be susceptible to prevention or treatment using compositions provided herein.

Recombinant monocyte-derived proteins or antibodies of the invention may be purified and then administered to a patient. These reagents can be combined for therapeutic use with additional active or inert ingredients, e.g., in conventional pharmaceutically acceptable carriers or diluents, e.g., immunogenic adjuvants, along with physiologically innocuous stabilizers and excipients. In particular, these may be useful in a vaccine context, where the antigen is combined with one of these therapeutic versions of agonists or antagonists. These combinations can be sterile filtered and placed into dosage forms as by lyophilization in dosage vials or storage in stabilized aqueous preparations. This invention also contemplates use of antibodies or binding fragments thereof, including forms which are not complement binding.

Drug screening using antibodies or receptor or fragments thereof can identify compounds having binding affinity to these monocyte-derived proteins, including isolation of associated components. Subsequent biological assays can then be utilized to determine if the compound blocks or antagonizes the activity of the protein. Likewise, a compound having intrinsic stimulating activity might activate the cell through the protein and is thus an agonist. This invention further contemplates the therapeutic use of antibodies to the proteins as antagonists.

The quantities of reagents necessary for effective therapy will depend upon many different factors, including means of administration, target site, physiological state of the patient, and other medicants administered. Thus, treatment dosages should be titrated to optimize safety and efficacy. Typically, dosages used in vitro may provide useful guidance in the amounts useful for in situ administration of these reagents. Animal testing of effective doses for treatment of particular disorders will provide further predictive indication of human dosage. Various considerations are described, e.g., in Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa. Methods for administration are discussed therein and below, e.g., for oral, intravenous, intraperitoneal, or intramuscular administration, transdermal diffusion, and others. Pharmaceutically acceptable carriers will include water, saline, buffers, and other compounds described, e.g., in the *Merck Index*, Merck & Co., Rahway, N.J. Dosage ranges would ordinarily be expected to be in amounts lower than 1 mM concentrations, typically less than about 10 µM concentrations, usually less than about 100 nM, preferably less than about 10 µM (picomolar), and most preferably less than about 1 fM (femtomolar), with an appropriate carrier. Slow release formulations, or a slow release apparatus will often be utilized for continuous administration.

The proteins, antagonists, and agonists could be administered directly to the host to be treated or, depending on the size of the compounds, it may be desirable to conjugate them to carrier proteins such as ovalbumin or serum albumin prior to their administration. Therapeutic formulations may be administered in many conventional dosage formulations. While it is possible for the active ingredient to be administered alone, it is preferable to present it as a pharmaceutical formulation. Formulations typically comprise at least one active ingredient, as defined above, together with one or more acceptable carriers thereof. Each carrier should be both pharmaceutically and physiologically acceptable in the sense of being compatible with the other ingredients and not injurious to the patient. Formulations include those suitable for oral, rectal, nasal, or parenteral (including subcutaneous, intramuscular, intravenous and intradermal) administration. The formulations may conveniently be presented in unit dosage form and may be prepared by any methods well known in the art of pharmacy. See, e.g., Gilman, et al. (eds.) (1990) *Goodman and Gilman's: The Pharmacological Bases of Therapeutics* (8th ed.) Pergamon Press; and (1990) *Remington's Pharmaceutical Sciences* (17th ed.) Mack Publishing Co., Easton, Pa.; Avis, et al. (eds.) (1993) *Pharmaceutical Dosage Forms: Parenteral Medications* Dekker, N.Y.; Lieberman, et al. (eds.) (1990) *Pharmaceutical Dosgae Forms: Tablets* Dekker, N.Y.; and Lieberman, et al. (eds.) (1990) *Pharmaceutical Dosage Forms: Disperse Systems* Dekker, N.Y. The therapy of this invention may be combined with or used in association with other chemotherapeutic or chemopreventive agents.

Many modifications and variations of this invention can be made without departing from its spirit and scope, as will be apparent to those skilled in the art. The specific embodiments described herein are offered by way of example only, and the invention is to be limited only by the terms of the appended claims, along with the full scope of equivalents to which such claims are entitled.

What is claimed is:

1. An antigen-antibody complex comprising:
   a) a purified antibody or antigen binding fragment thereof that specifically binds an FDF03-S1 polypeptide consisting of the amino acid sequence of SEQ ID NO: 6; and
   b) said FDF03-S1 polypeptide.

2. The antigen-antibody complex of claim 1, wherein said antibody is a monoclonal antibody.

3. The antigen-antibody complex of claim 1, wherein said antigen binding fragment is a Fab, Fv or antibody half molecule.

4. An antigen-antibody complex comprising:
   a) a purified antibody or antigen binding fragment thereof that specifically binds an FDF03-S1 polypeptide consisting of the amino acid sequence of residues 1-210 of SEQ ID NO: 6; and
   b) said FDF03-S1 polypeptide.

5. The antigen-antibody complex of claim 4, wherein said antibody is a monoclonal antibody.

6. The antigen-antibody complex of claim 4, wherein said antigen binding fragment is a Fab, Fv or antibody half molecule.

* * * * *